US012245956B2

(12) United States Patent
Herr et al.

(10) Patent No.: US 12,245,956 B2
(45) Date of Patent: Mar. 11, 2025

(54) PERIPHERAL NEURAL INTERFACE VIA NERVE REGENERATION TO DISTAL TISSUES

(71) Applicant: Massachusetts Institute of Technology, Cambridge, MA (US)

(72) Inventors: Hugh M. Herr, Concord, NH (US); Ronald R. Riso, Carlisle, MA (US); Katherine W. Song, Sunnyvale, CA (US); Richard J. Casler, Jr., Los Gatos, CA (US); Matthew J. Carty, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 36 days.

(21) Appl. No.: 17/120,938

(22) Filed: Dec. 14, 2020

(65) Prior Publication Data

US 2021/0093470 A1    Apr. 1, 2021

Related U.S. Application Data

(60) Continuation of application No. 15/233,241, filed on Aug. 10, 2016, now Pat. No. 10,898,351, which is a
(Continued)

(51) Int. Cl.
*A61F 2/72* (2006.01)
*A61B 5/24* (2021.01)
(Continued)

(52) U.S. Cl.
CPC ............... *A61F 2/72* (2013.01); *A61F 2/68* (2013.01); *A61N 1/0551* (2013.01);
(Continued)

(58) Field of Classification Search
CPC ........................................................ A61F 2/72
See application file for complete search history.

(56) References Cited

U.S. PATENT DOCUMENTS 3,735,425 A    5/1973    Hoshall et al.
4,750,499 A    6/1988    Hoffer et al.
(Continued)

FOREIGN PATENT DOCUMENTS

CA         2858824 C  *  5/2020  ......... A61N 1/36003
WO    WO 1985/005548 A1    12/1985
(Continued)

OTHER PUBLICATIONS

Agnew et al., "Histologic and physiologic evaluation of electrically stimulated peripheral nerve: Considerations for the selection of parameters," Annals of Biomedical Engineering, vol. 17, pp. 39-60, 1989.
(Continued)

*Primary Examiner* — Jacqueline Woznicki
(74) *Attorney, Agent, or Firm* — Hamilton, Brook, Smith & Reynolds, P.C.

(57) ABSTRACT

At least partial function of a human limb is restored by surgically removing at least a portion of an injured or diseased human limb from a surgical site of an individual and transplanting a selected muscle into the remaining biological body of the individual, followed by contacting the transplanted selected muscle, or an associated nerve, with an electrode, to thereby control a device, such as a prosthetic limb, linked to the electrode. Simulating proprioceptive sensory feedback from a device includes mechanically linking at least one pair of agonist and antagonist muscles, wherein a nerve innervates each muscle, and supporting each pair with a support, whereby contraction of the agonist muscle of each pair will cause extension of the paired antagonist muscle. An electrode is implanted in a muscle of
(Continued)

each pair and electrically connected to a motor controller of the device, thereby simulating proprioceptive sensory feedback from the device.

23 Claims, 20 Drawing Sheets

Related U.S. Application Data division of application No. 14/520,766, filed on Oct. 22, 2014, now Pat. No. 9,474,634.

(60) Provisional application No. 62/019,266, filed on Jun. 30, 2014, provisional application No. 61/894,040, filed on Oct. 22, 2013.

(51) Int. Cl.
    *A61B 5/389*     (2021.01)
    *A61F 2/68*     (2006.01)
    *A61N 1/05*     (2006.01)
    *A61N 1/36*     (2006.01)
    *A61B 5/00*     (2006.01)
    *A61B 17/11*     (2006.01)
    *A61F 2/48*     (2006.01)
    *A61F 2/60*     (2006.01)

(52) U.S. Cl.
CPC ........ *A61N 1/36003* (2013.01); *A61B 5/0028* (2013.01); *A61B 5/0031* (2013.01); *A61B 5/24* (2021.01); *A61B 5/389* (2021.01); *A61B 5/40* (2013.01); *A61B 5/4029* (2013.01); *A61B 5/4041* (2013.01); *A61B 5/4047* (2013.01); *A61B 5/4052* (2013.01); *A61B 5/441* (2013.01); *A61B 5/45* (2013.01); *A61B 5/48* (2013.01); *A61B 5/4824* (2013.01); *A61B 5/4827* (2013.01); *A61B 5/4851* (2013.01); *A61B 5/68* (2013.01); *A61B 5/6801* (2013.01); *A61B 5/6846* (2013.01); *A61B 17/1128* (2013.01); *A61B 2017/1135* (2013.01); *A61F 2/482* (2021.08); *A61F 2002/607* (2013.01); *A61F 2002/6827* (2013.01); *A61F 2002/6872* (2013.01)

(56) References Cited

U.S. PATENT DOCUMENTS

| | | | |
|---|---|---|---|
| 5,158,097 A | 10/1992 | Christlieb | |
| 5,769,875 A | 6/1998 | Peckham et al. | |
| 5,824,027 A | 10/1998 | Hoffer et al. | |
| 6,456,866 B1 | 9/2002 | Tyler et al. | |
| 7,260,436 B2 | 8/2007 | Kilgore et al. | |
| 7,367,958 B2 | 5/2008 | McBean et al. | |
| 7,396,337 B2 | 7/2008 | McBean et al. | |
| 7,725,175 B2 * | 5/2010 | Koeneman | A61H 1/02 600/595 |
| 7,936,337 B2 | 5/2011 | Fux et al. | |
| 9,352,146 B2 | 5/2016 | Langhals et al. | |
| 9,474,634 B2 | 10/2016 | Herr et al. | |
| 10,376,389 B2 | 8/2019 | Gaston et al. | |
| 2003/0144710 A1 | 7/2003 | Haugland et al. | |
| 2004/0106881 A1 | 6/2004 | McBean et al. | |
| 2004/0111130 A1 | 6/2004 | Hrdlicka et al. | |
| 2006/0167564 A1 * | 7/2006 | Flaherty | G06F 3/011 623/57 |
| 2006/0224203 A1 * | 10/2006 | Hettrick | A61N 1/3627 607/19 |
| 2007/0038311 A1 | 2/2007 | Kuikn | |
| 2007/0191743 A1 | 8/2007 | McBean et al. | |
| 2008/0139968 A1 | 6/2008 | Endo et al. | |
| 2008/0228240 A1 | 9/2008 | Edell et al. | |
| 2008/0234781 A1 | 9/2008 | Einav et al. | |
| 2008/0243216 A1 | 10/2008 | Zilberman et al. | |
| 2009/0221896 A1 | 9/2009 | Rickert et al. | |
| 2009/0292325 A1 | 11/2009 | Cederna et al. | |
| 2011/0257501 A1 | 10/2011 | Huys et al. | |
| 2013/0253606 A1 | 9/2013 | Youn et al. | |
| 2013/0304174 A1 | 11/2013 | Langhals | |
| 2014/0005763 A1 | 1/2014 | Cederna et al. | |
| 2014/0058495 A1 | 2/2014 | Sakai et al. | |
| 2014/0067083 A1 * | 3/2014 | Wenstrand | A61F 2/583 623/24 |
| 2015/0173918 A1 | 6/2015 | Herr et al. | |
| 2016/0051383 A1 | 2/2016 | Goldfarb et al. | |
| 2016/0346099 A1 | 12/2016 | Herr et al. | |

FOREIGN PATENT DOCUMENTS

| | | |
|---|---|---|
| WO | WO 2012/097297 A2 | 7/2012 |
| WO | 2013150298 A1 | 10/2013 |
| WO | WO 2015/061453 A1 | 4/2015 |

OTHER PUBLICATIONS

Aitken, "The effect of peripheral connexions on the maturation of regenerating nerve fibres", Journal of Anatomy, vol. 83, No. 1, pp. 32-43, 1949.

Akin, T., et al., "A Micromachined Silicon Sieve Electrode for Nerve Regeneration Applications," IEEE Transactions on Biomedical Engineering, 41(4): 305-313 (1994).

International Search Report and Written Opinion of the International Searching Authority from International Application No. PCT/US2014/061773, "Peripheral Neural Interface Via Nerve Regeneration to Distal Tissues," mailed Jan. 7, 2015.

International Preliminary Report on Patentability for PCT/US2014/061773, entitled "Peripheral Neural Interface Via Nerve Regeneration to Distal Tissues," Date of mailing Apr. 26, 2016.

Au, S. K., et al., "Powered Ankle-Foot Prosthesis Improves Walking Metabolic Economy," IEEE Transactions on Robotics, 25(1): 51-66 (2009).

Biewener, Biomechanics: Structures and Systems, Oxford Univ. Press, Oxford, New York, Tokyo, Title Page and Table of Contents, (1992).

Bradley et al., "Functional regeneration of glossopharyngeal nerve through micromachined sieve electrode arrays," Brain Research, vol. 594, No. 1, pp. 84-90, 1992.

Bradley et al., "Long term chronic recordings from peripheral sensory fibers using a sieve electrode array," Journal of Neuroscience Methods, vol. 73, No. 2, pp. 177-186, 1997.

Branner et al., "A multielectrode array for intrafascicular recording and stimulation in sciatic nerve of cats," Brain Research Bulletin, vol. 51, No. 4, pp. 293-306, 2000.

Brindley, G. S., et al., "Sacral anterior root stimulators for bladder control in paraplegia: the first 50 cases," Journal of Neurology, Neurosurgery, and Psychiatry, 49(10): 1104-1114 (1986).

Cravioto et al., "Clinical and ultrastructural study of painful neuroma", Neurosurgery, vol. 8, No. 2, pp. 181-190, 1981.

De Luca, C. J., "Surface Electromyography: Detection and Recording, " DelSys Incorporated, (2002).

Dellon et al., "Treatment of the painful neuroma by neuroma resection and muscle implantation", Plastic and Reconstructive Surgery, vol. 77, No. 3, pp. 427-438, 1986.

Dodson et al. "Case study: surgical prosthetic and therapeutic considerations for a patient with ipsilateral brachia! plexus injury and transradial amputation", Aug. 14, 2011, MyoElectric Controls/Powered Prosthetics Symposium, Fredericton, New Brunswick, Canada (Year: 2011).

Dumanian et al. "Targeted reinnervation for transhumeral amputees: current surgical technique and update on results". Plastic Reconstructive Surgery 124: 863. 2009 (Year: 2009).

Edell et al., "Bi-directional peripheral nerve interface for the control of powered prosthetic limbs," DARPA Contract N6600 1-05-C-8030, 2006.

(56) References Cited

OTHER PUBLICATIONS

Edell, "A peripheral nerve information transducer for amputees: long-term multichannel recordings from rabbit peripheral nerves," IEEE Transactions on Biomedical Engineering, vol. 33, No. 2,pp. 203-214, 1986.
Edin et al., "Finger movement responses of cutaneous mechanoreceptors in the dorsal skin of the human hand," Journal of Neurophysiology, vol. 65, pp. 657-670, 1991.
Farnsworth, "Wireless Implantable EMG Sensing Microsystem." Master's thesis, Case Western Reserve University (2010).
Fitzgerald et al., "Microchannels as axonal amplifiers," IEEE Transactions on Biomedical Engineering, vol. 55, No. 3, pp. 1136-1146, 2008.
Fitzgerald et al., "A regenerative microchannel neural interface for recording from and stimulating peripheral axons in vivo," Journal of Neural Engineering, vol. 9, No. 1, pp. 1-13, 2012.
Forrest et al. "Use of the Case Western Reserve Veterans Administration neuroprosthesis for exercise, standing and transfers by a paraplegic subject," Disability and Rehabilitation Assistive Technology, vol. 7, No. 4, pp. 340-344, 2012.
Frost et al., "Neuroprosthetic hand real-time proportional control by rodent regenerative peripheral nerve interfaces," Plastic & Reconstructive Surgery, vol. 133, No. 4S,pp. 1012-1013, 2014.
Gaston et al. "A novel muscle transfer for independent digital control of a myoelectric prosthesis: the starfish procedure". Journal of Hand Surgery Am. Apr. 3, 2018. (Year: 2018).
Grandjean et al., "Recruitment properties of monopolar and bipolar epimysial electrodes," Annals of Biomedical Engineering, vol. 14, No. 1, pp. 53-66, 1986.
Haugland et al., "Cutaneous whole nerve recordings used for correction of foot drop in hemiplegic man," IEEE Transactions on Biomedical Engineering, vol. 3, No. 4, pp. 307-317, 1995.
Haugland et al, "Restoration of lateral hand grasp using natural sensors," Artificial Organs, vol. 21, No. 3, pp. 250-253, 1997.
"Herr ""The new bionics that let usrun, climb and dance"", TED 2014; Filmed Mar. 2014; Available at: https://www.ted.com/talks/hugh_herr_the_new_bionics_that_let_us_run_climb_and_dance (Retrieved from the Internet on Apr. 15, 2015)."
Herr et al., "Bionic ankle-foot prosthesis normalizes walking gait for persons with leg amputation," Proc. R. Soc. B, 279(1728): 457-464 (2012).
Hijjawi et al. "Improved myoelectric prosthesis control accomplished using multiple nerve transfers" Plastic Reconstructive Surgery 118: 1573. 2006. (Year: 2006).
Hoffer et al., "Roles of muscle activity and load on the relationship between muscle spindle length and whole muscle length in the freely walking cat," Prog. Brain Res., 80: 75 (1989).
Hulliger, "The mammalian muscle spindle and its central control," Reviews of Physiology, Biochemishy and Phamacology, vol. 101, pp. 1-110, 1984.
Jezernik et al., "Detection and inhibition of hyperreflexia-like bladder contractions in the cat by sacral nerve root recording and electrical stimulation," Neurourology and Urodynamics, vol. 20, No. 2, pp. 215-230, 2001.
Kantrowitz et al. Development of a percutaneous energy transmission system, annual report prepared for Devices and Technology Branch, Division of Heart and Vascular Diseases, Natl Heart Lung and Blood Institute: Apr. 16, 1979. 70 pages.
Kantrowitz et al. Development of a percutaneous energy transmission system, annual report prepared for Devices and Technology Branch, Division of Heart and Vascular Diseases, Nall Heart Lung and Blood Institute: May 27, 1982. 47 pages.
Kantrowitz A., et al. Development of a percutaneous energy transmission system, annual report prepared for Devices and Technology Branch, Division of Heart and Vascular Diseases, Natl Heart Lung and Blood Institute: Jun. 5, 1983. 76 pages.
Kim et al., "Materials for multifunctional balloon catheters with capabilities in cardiac electrophysiological mapping and ablation therapy," Nature Materials, vol. 10, pp. 316-323, 2011.
Kovacs et al., "Regeneration microelectrode array for peripheral nerve recording and stimulation," IEEE Transactions on Biomedical Engineering, vol. 39,No. 9,pp. 893-902, 1992.
Kuiken et al., "The effect of subcutaneous fat on myoelectric signal amplitude and cross-talk," Prosthetics and Orthotics International, 27(1): 48-54 (2003).
Kuiken et al., "Targeted Muscle Reinnervation for Real-time Myoelectric Control of Multifunction Artificial Arms," JAMA, 301 (6): 619-628 (2009).
Kuiken, "Targeted reinnervation for improved prosthetic function," Physical Medicine and Rehabilitation Clinics of North America, vol. 17, No. 1, pp. 1-13, 2006.
Kuiken et al., "The use of targeted muscle reinnervation for improved myoelectric prosthesis control in a bilateral shoulder disarticulation amputee," Prosthetics and Orthontics International, 28: 245-253 (2004).
Kuiken et al. "Targeted reinnervation for enhanced prosthetic arm function in a woman with a proximal amputation: a case study". The Lancet. vol. 369 pp. 371-380. Feb. 3, 2007. (Year: 2007).
Lacour et al., "Long micro-channel electrode arrays: a novel type of regenerative peripheral nerve interface," IEEE Transactions on Neural Systems and Rehabilitation Engineering, vol. 17, No. 5, pp. 454-460, 2009.
Larson et al., "Prototype sensory regenerative peripheral nerve interface for artificial limb somatosensory feedback," Plastic & Reconstructive Surgery, vol. 133, No. 3S,pp. 26-27,2014.
Lawrence et al., "Long-term biocompatibility of implanted polymer-based intrafascicular electrodes," Journal of Biomedical Materials Research, vol. 63, No. 5, pp. 501-506, 2002.
Leevering, K., P950035. Premarket Approval of NeuroControl Corporation Freehand System. CDRH (Aug. 15, 1997).
Loeb, "Cochlear prosthetics," Annual Review of Neuroscience, vol. 13, pp. 357-371, 1990.
Malagodi et al., "An intrafascicular electrode for recording of action potentials in peripheral nerves," Annals of Biomedical Engineering, vol. 17, pp. 397-410, 1989.
Martinez-Villalpando et al., "Agonist-antagonist active knee prosthesis: A preliminary study in level-ground walking," Journal of Rehabilitation Research & Development, 46(3): 361-374 (2009).
Martini, R., et al., "The L2/HNK-1 Carbohydrate Is Preferentially Expressed by Previously Motor Axon-associated Schwann Cells in Reinnervated Peripheral Nerves," The Journal of Neuroscience, 14(11): 7180-7191 (1994).
Naples et al., "A spiral nerve cuff electrode for peripheral nerve stimulation," IEEE Transactions on Biomedical Engineering, vol. 35, No. 11, pp. 905-916, 1988.
Navarro et al., "Stimulation and recording from regenerated peripheral nerves through polyimide sieve electrodes," Journal of the Peripheral Nervous System, vol. 3, No. 2, pp. 91-101, 1998.
New device gives heart failure patients more freedom, UChicago Medicine, Oct. 30, 2000, 6 pages.
Ochoa et al . . . , "Sensations Evoked by Intraneural Microstimulation of Single Mechanoreceptor Units Innervating the Human Hand," J. Physiol., 342: 633-654 (1983).
Okuda, T., et al., "The Autotomy Relief Effect of a Silicone Tube Covering the Proximal Nerve Stump," J. Orthop. Res., 24(7): 1427-1437 (2006).
Riso et al., "Nerve cuff recordings of muscle afferent activity from tibial and peroneal nerves in rabbit during passive ankle motion," IEEE Transactions on Rehabilitation Engineering, vol. 8, No. 2, pp. 244-258, 2000.
Roberts, et al., "Muscular Force in Running Turkeys: The Economy of Minimizing Work," Science, 275(5303): 1113-1115 (1997).
Roll et al., "Kinesthetic role of muscle afferents in man, studied by tendon vibration and microneurography," Experimental Brain Research, vol. 4 7, No. 2, pp. 177-190, 1982.
Rouse et al., "Clutchable Series-Elastic Actuator: Design of a Robotic Knee Prosthesis for Minimum Energy Consumption," Proceedings of the IEEE International Conference on Rehabilitation Robotics (2013).
Sahin et al., "Chronic recordings of hypoglossal nerve activity in a dog model of upper airway obstruction," J. Appl. Physiol., 87(6): 2197-2206 (1999).

(56) References Cited

OTHER PUBLICATIONS

Schuettler et al., "18polar hybrid cuff electrodes for stimulation of peripheral nerves," in Proceedings of the International Functional Electrical Stimulation Society, Aalborg, Denmark, pp. 265-268, 2000.
Sosa et al., "Immunosuppressants: Neuroprotection and promoting neurological recovery following peripheral nerve and spinal cord lesions," Experimental Neurology, vol. 195, pp. 7-15, 2005.
Stevanovic et al. "Functional Free muscle transfer for upper extremity reconstruction". Aug. 2014 Plastic Reconstructive Surgery 134: 257e (Year: 2014).
Taylor et al., "The functional impact of the Freehand System on tetraplegic hand function," Clinical Results. Spinal cord, 40(11): 560-6 (2002).
Tian et al., "Macroporous nanowire nanoelectronic scaffolds for synthetic tissues," Nature Materials, vol. 11, pp. 986-994, 2012.
Urbanchek et al., "Regenerative peripheral nerve interface function at 1 and 3 months after implantation," Plastic & Reconstructive Surgery, vol. 130, No. IS, pp. 84, 2012.
Vallbo, "Basic patterns of muscle spindle discharges in man," in Muscle Receptors and Movement, A. Taylor and A. Prochazka, Eds. London: Macmillan, 1981, pp. 263-275.
Venkatramani et al. "Role of free functioning muscle transfer in improving the functional outcomes following replantation of crush avulsion amputations of the forearm." Department of Plastic, Hand and Reconstructive Microsurgery, Ganga Hospital, Coimbatore, India. S105-S110. 2019. (Year: 2019).
Veraart et al., "Pattern recognition with the optic nerve visual prosthesis," Artificial Organs, vol. 27, No. 11, pp. 996-1004, 2003.
Veraart et al., "Selective control of muscle activation with a multipolar nerve cuff electrode," IEEE Transactions on Biomedical Engineering, vol. 40, No. 7, pp. 640-653, 1993.
Vrbova et al., "Chemical communication between regenerating motor axons and Schwann cells in the growth pathway," European Journal of Neuroscience, vol. 30, No. 3, pp. 366-375, 2009.
Wallman et al., "The geometric design of micromachined silicon sieve electrodes influences functional nerve regeneration," Biomaterials, vol. 22, No. 10, pp. 1187-1193, 2001.
Wallman et al., "Perforated silicon nerve chips with doped registration electrodes: in vitro performance and in vivo operation," IEEE Transactions on Biomedical Engineering, vol. 46, No. 9, pp. 1065-1073, 1999.
Walmsley et al., "Forces Produced by Medical Gastrocnemius and Soleus Muscles During Locomotionin Freely Moving Cats," J. Neurophysiol. vol. 41, No. 5, (1978), pp. 1203-1216.
Weir et al., "Implantable Myoelectric Sensors (IMESs) for Intramuscular Electromyogram Recording," IEEE Transactions on Biomedical Engineering, 56(1): 159-171 (2009).
Yoshida et al., "Peripheral nerve recording electrodes and techniques," in Neuroprostheses in Theory and Practice vol. 2, K. W. Horeb and G. S. Dhillon, Eds. Hakensack, NJ: World Scientific, 2004, pp. 683-744.
Yoshida et al., "Characterization of signals and noise rejection with bipolar longitudinal intrafascicular electrodes," IEEE Transactions on Biomedical Engineering, vol. 46, No. 2, pp. 226-234, 1999.
International Search Report and Written Opinion for International Application No. PCT/US2017/012553, entitled "Method and System for Providing Proprioceptive Feedback and Functionality Mitigating Limb Pathology," dated Jun. 16, 2017.

\* cited by examiner

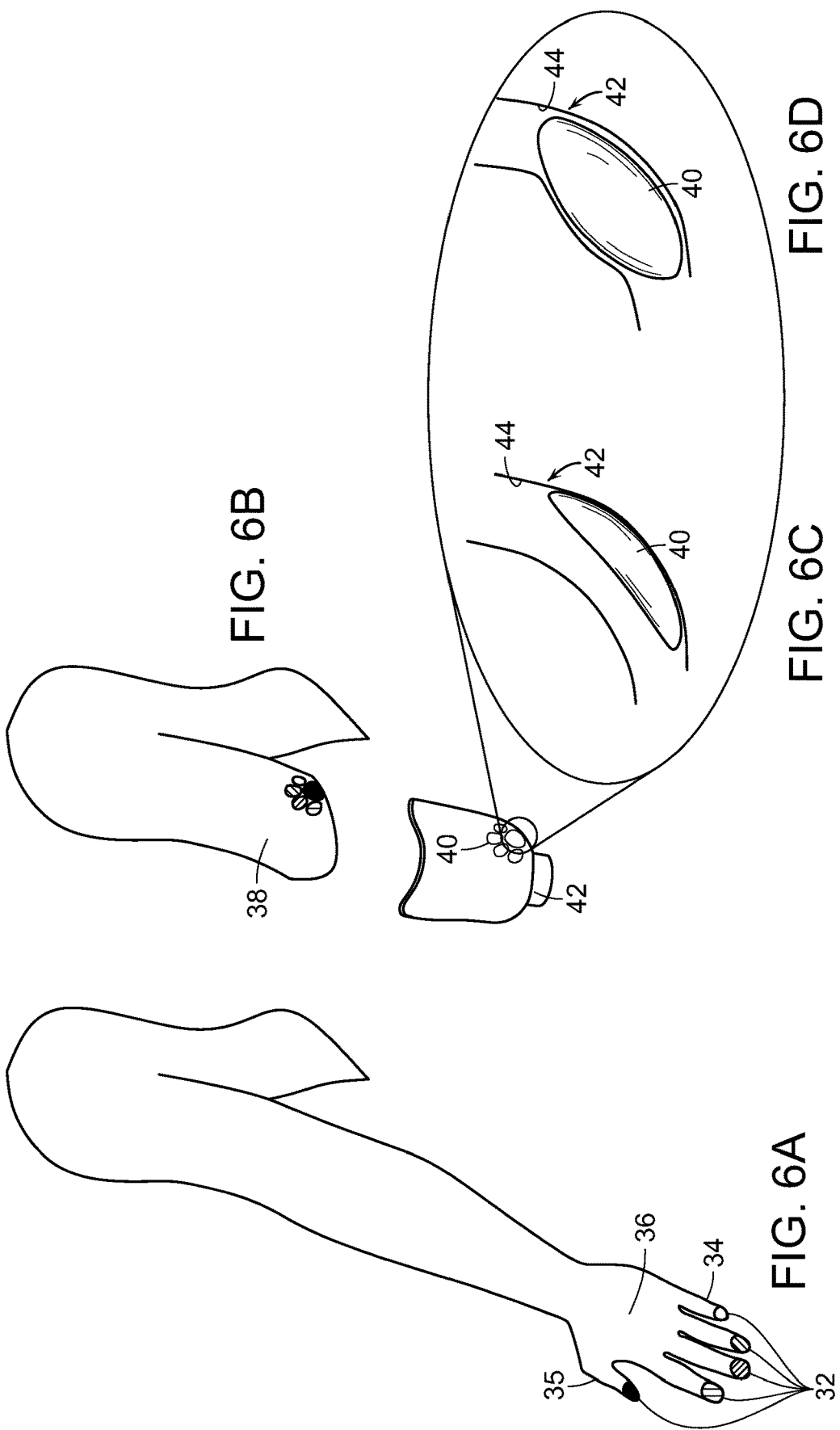

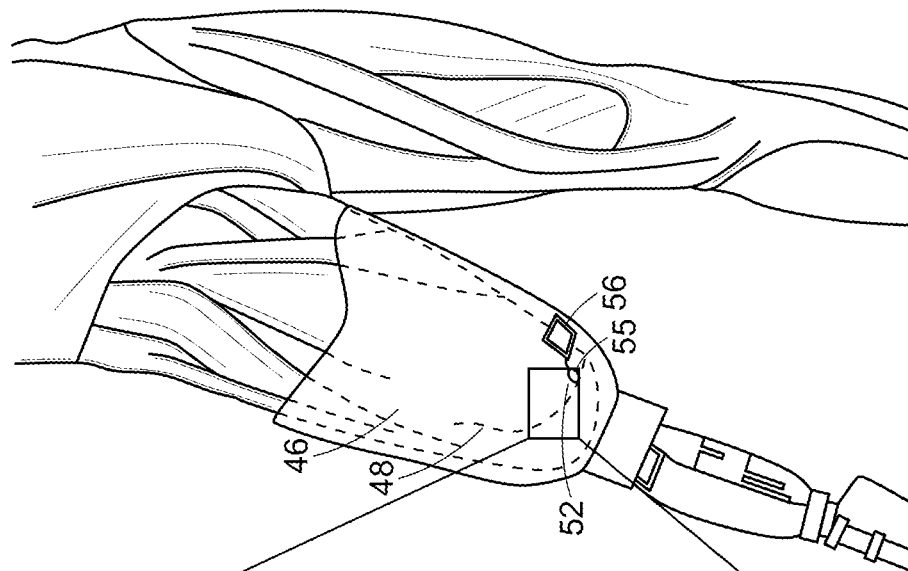
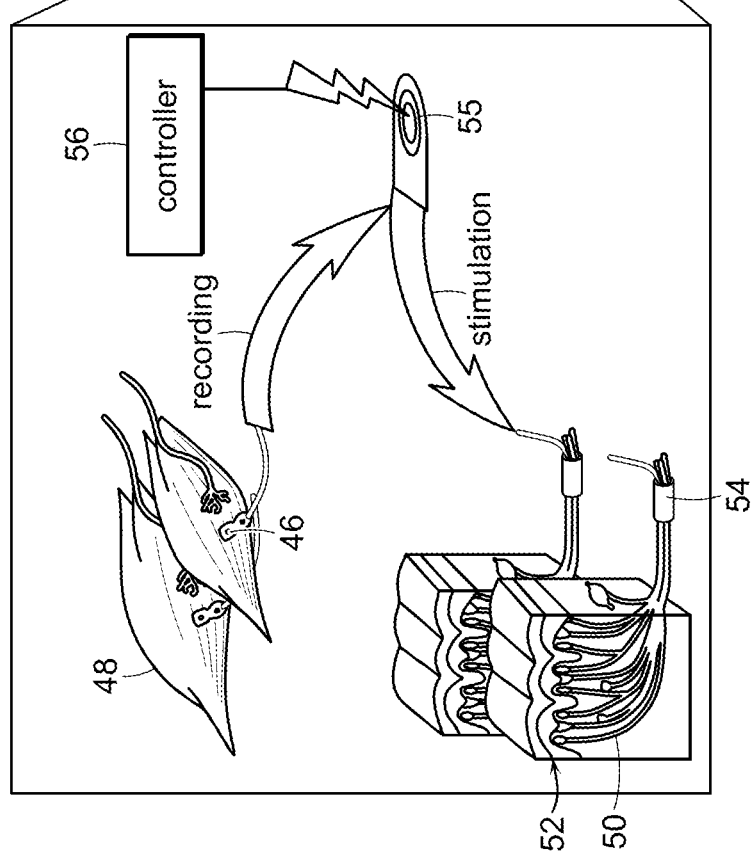
FIG. 7A
FIG. 7B

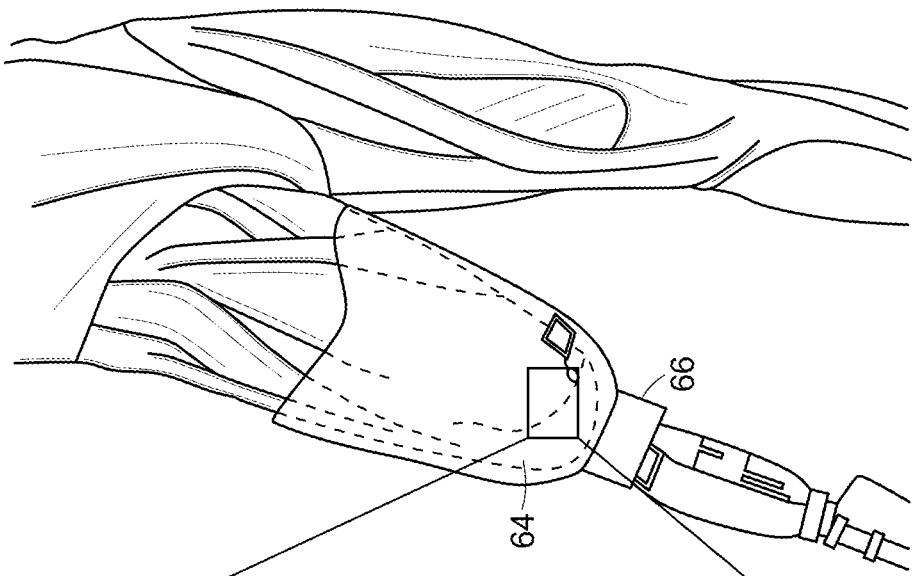
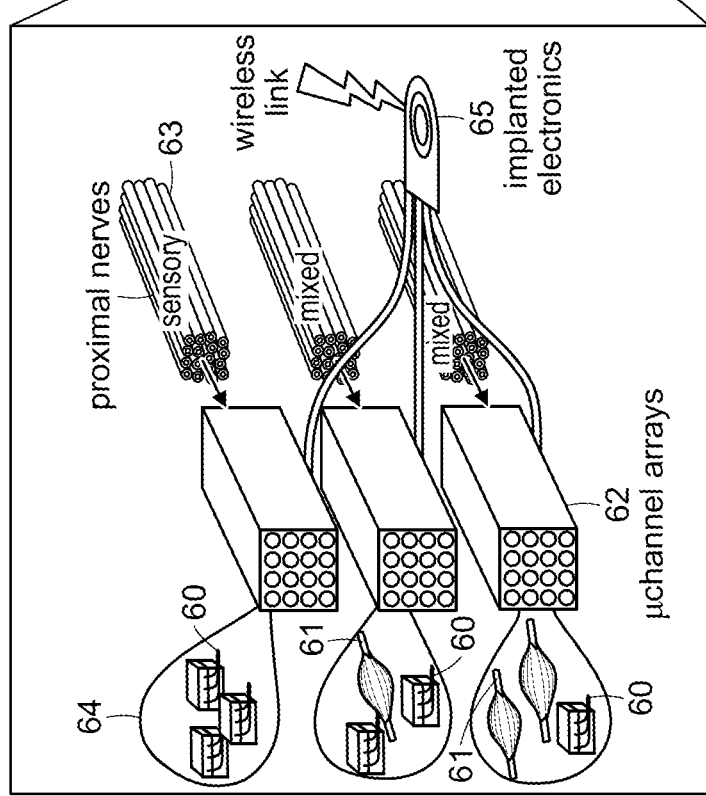
FIG. 8A
FIG. 8B

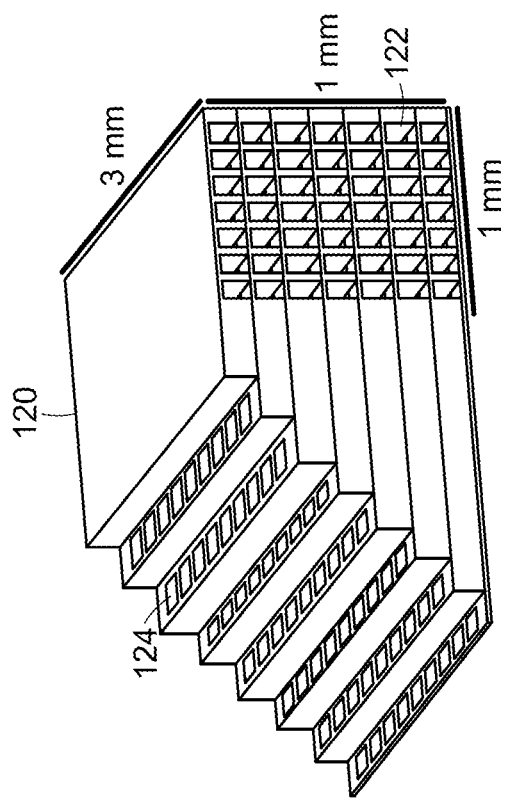
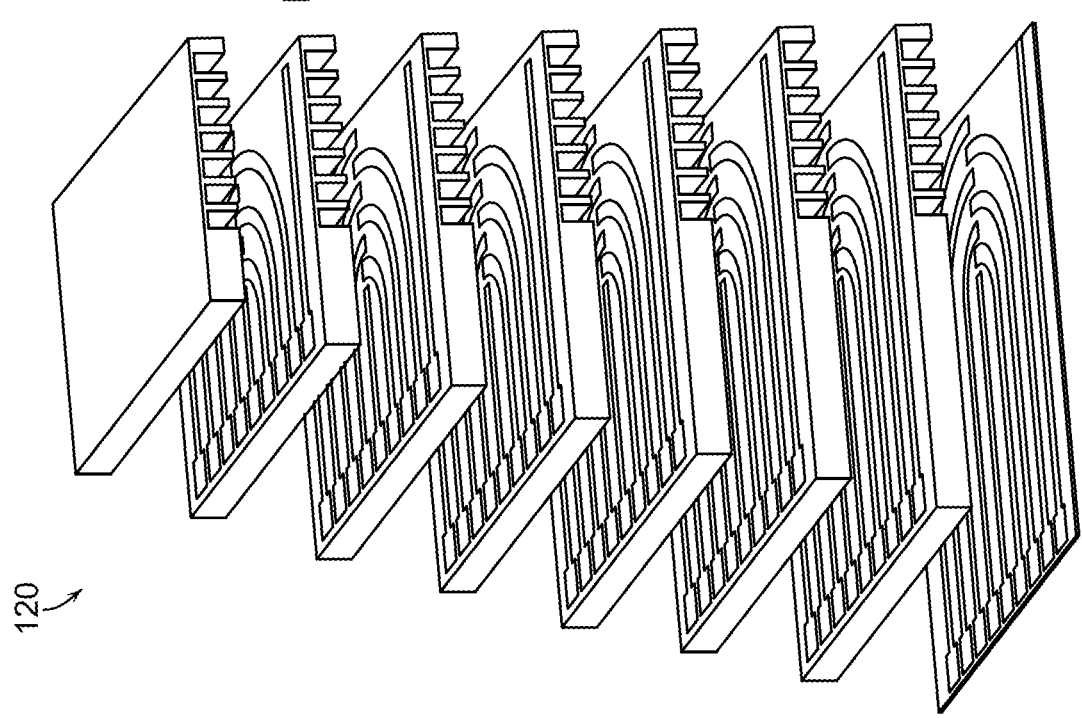
FIG. 13B
FIG. 13A

PERIPHERAL NEURAL INTERFACE VIA NERVE REGENERATION TO DISTAL TISSUES

RELATED APPLICATIONS

This application is a continuation of U.S. application Ser. No. 15/233,241, filed Aug. 10, 2016, which is a divisional of U.S. application Ser. No. 14/520,766, filed Oct. 22, 2014, now U.S. Pat. No. 9,474,634, issued Oct. 25, 2016, which claims the benefit of U.S. Provisional Application No. 61/894,040, filed on Oct. 22, 2013, and U.S. Provisional Application No. 62/019,266, filed on Jun. 30, 2014. The entire teachings of the above applications are incorporated herein by reference.

BACKGROUND OF THE INVENTION

Recent advances in prosthetic limbs include the provision of multiple degrees of freedom as well as powered actuators that have the potential to provide substantially greater functionality than the passive devices that existed just a decade ago. Despite these engineering accomplishments, developers still struggle with the issue of how to provide the prosthesis user with methods for coordinating the simultaneous control of all of the joints that are involved with, for example, object manipulation in the upper extremity case, or standing and walking in the lower extremity case. This deficit was first apparent for upper extremity prostheses, which now can provide elbow function, wrist rotation, and hand opening and closing. Today's commercially available, upper-extremity prosthetic controllers make use of the EMG activity (electro-myographic activity generated by muscle contraction) of functional native muscles that are present in the amputee's residual limb. This approach allows for proportional control with minimal execution delay. When the EMG activity used for prosthetic control arises from a pair of antagonistic muscles that would normally move the homologous biological joint (e.g., the biceps and triceps controlling flexion and extension, respectively, of the prosthesis elbow joint), the neurally controlled EMG commands are completely intuitive and thus easy to master.

However, more commonly in practice, the same set of EMG signal sources are used to control additional prosthetic joints, and this requires that the command sources be switched among the assigned joints in a serial manner. The resulting motion for most activities is thus awkward, time consuming, and tedious, since it breaks up any compound arm and hand movement into serial positioning steps, resulting in poor utilization of powered prostheses. In the lower extremity, powered ankle and knee joints are just becoming available to the general population. However, commercial lower-extremity prostheses typically do not utilize EMG as a source of control signals. Artificial sensory and computational systems have been demonstrated to provide some degree of control over ankle and knee flexion and extension for powered leg prostheses (E. C. Martinez-Villalpando and H. M. Herr, "Agonist-antagonist active knee prosthesis: A preliminary study in level-ground walking," Journal of Rehabilitation Research & Development (JRRD), vol. 46, no. 3, pp. 361-73, 2009; S. Au, J. Weber, and H. M Herr, "Powered Ankle-Foot Prosthesis Improves Walking Metabolic Economy," IEEE Transactions on Robotics, vol. 25, no. 1, pp. 51-66, 2009; H. M. Herr and A. M. Grabowski, "Bionic ankle-foot prosthesis normalizes walking gait for persons with leg amputation," Proceedings of the Royal Society B, vol. 279, no. 1728, pp. 457-464, February 2012; E. J. Rouse, L. M. Mooney, E. C. Martinez-Villalpando, and H. M. Herr, "A clutchable series-elastic actuator: design of a robotic knee prosthesis for minimum energy consumption," Proceedings of the IEEE International Conference on Rehabilitation Robotics, 2013). It is well appreciated, however, that the next generation of devices should provide smooth, simultaneous volitional-neural control over several degrees of freedom, such as the knee, ankle and subtalar joints. In that case, simultaneous control of several degrees of freedom will require multiple sources of independent, reliable, and intuitive control that can best be obtained by interfacing with the amputee's extrinsic neural control.

The efficacy of using an EMG-based neural activity approach for achieving simultaneous control of multiple prosthetic joints has been demonstrated in principle by a technique now referred to as "Targeted Muscle Re-innervation," or TMR (T. A. Kuiken, G. A. Dumanian, R. D. Lipschutz, L. A. Miller, K. A. Stubblefield, "The use of targeted muscle reinnervation for improved myoelectric prosthesis control in a bilateral shoulder disarticulation amputee, Prosthetics and Orthotics International, vol. 28, pp. 245-53, 2004; T. A. Kuiken, "Targeted reinnervation for improved prosthetic function," Physical Medicine and Rehabilitation Clinics of North America, vol. 17, no. 1, pp. 1-13, 2006). For transhumeral prosthetic control, for example, TMR utilizes the activity of all four of the arm trunk nerves. As a surgical procedure, each trunk nerve is mobilized from the brachial plexus, and each nerve is anastomosed to a separate division of the pectoralis major muscle of the chest. The nerves grow into and innervate their respective new muscle targets and can independently cause contractions of the respectively innervated pectoral muscle divisions. The four recorded muscle signals can then be assigned to prosthetic elbow, wrist, and hand functions according to the original natural hand control function of each of the translocated nerves. For example, hand closing is controlled by evoked EMG activity from the pectoral muscle division innervated by the median nerve, and hand opening is controlled by EMG activity from the muscle division innervated by the radial nerve. Essentially, the operator's brain performs the coordination of the prosthesis joints when a complex task is performed. Despite the laudable success of the original and ensuing demonstrations, the TMR approach has a few shortcomings; for instance, the native innervation of the pectoral muscle (or other selected host muscle) must be removed so that the normal activation of the host muscle by its native innervation does not interfere with that by the transferred nerves. Having to eliminate the functionality of any native tissue for the greater good is not optimal. There are also some limitations regarding how far away a given nerve can be moved in order to connect it to a suitable muscle target. Finally, the use of surface recorded EMG and contiguous muscle targets can lead to inconsistent signal amplitudes and objectionable channel crosstalk (T. A. Kuiken, M. M. Lowery, and N. S. Stoykov, "The effect of subcutaneous fat on myoelectric signal amplitude and crosstalk," Prosthetics and Orthotics International, vol. 27, no. 1, pp. 48-54, 2003). This last issue has been addressed by using a large array of recording sites and performing substantial pattern recognition to interpret a user's intended movements unambiguously. Over time, however, it is still necessary to "re-tune" the system, which is a substantial inconvenience.

Therefore, there is a need for a method of reversing motor impairment of a human limb, and of restoring at least partial function of a human limb that overcomes or minimizes the above-referenced problems.

SUMMARY OF THE INVENTION

The invention generally is directed to a method of restoring at least partial function of a human limb, to reversing motor impairment of a human limb, to simulating proprioceptive sensory feedback from a device, and to simulate cutaneous sensory feedback from a device.

In one embodiment, the method of restoring at least a partial function of the human limb includes surgically removing from a surgical site at least a portion of an injured or diseased human limb from an individual, leaving intact at least one selected muscle from the damaged portion of the human limb, including at least one of blood vessels and nerves associated with that portion of the at least one selected muscle. The at least one selected muscle is transplanted into the remaining biological body of the individual and the at least one transplanted selected muscle, or associated nerve, is contacted with an electrode, whereby signals can be transmitted to and from at least one of the nerve and its associated transplanted muscle to thereby control a device linked to the electrode and extending from the surgical site, thereby restoring at least partial function of the human limb. Examples of suitable devices for use with the method of the invention include a prosthetic limb, an orthotic limb and an exoskeletal limb.

In a specific embodiment, and at least one patch of skin is dissected, wherein the patch of skin includes at least one nerve selected from the group consisting of an intact native sensory nerve and a new regenerative innervation nerve. The patch of skin is translocated onto a non-anatomical portion of the individual from which the limb was removed. The translocated patch is contacted with an external prosthetic socket of a prosthetic limb, the prosthetic socket including at least one component that provides mechanical stimulation to the translocated patch of skin. In another embodiment, that further includes the steps of contacting the nerve of the patch of skin with a nerve cuff, wherein the nerve cuff is linked to a controller. The nerve is selectively stimulated by actuating the nerve with the controller. In another embodiment, the nerve includes at least one sensory nerve selected from the group consisting of sural, saphenous, tibial, peroneal, median, ulnar, and radial nerves. In still one embodiment, contact in the nerves of the transplanted selected muscles with an electrode includes implanting electrode on the epimysium of the selected muscle or intramuscularly in the selected muscles.

In another embodiment, the method of reversing impairment of a human limb includes transecting a nerve associated with the impairment of the limb of an individual to thereby form proximal and distal ends of the transected nerve. The proximal and distal ends of the transected nerve are placed into proximal and distal ends of a microchannel array, thereby causing the nerve to regenerate through the microchannel array. Sensory afferent information of the regenerated nerve is recorded using sensing electrodes within a plurality of afferent microchannels of the microchannel array. Motor efferent information is stimulated to provide efferent motor stimulus to the nerve using stimulating electrodes within the plurality of efferent microchannels of the microchannel array. The stimulating electrodes are electrically connected to a motor controller of a device. The sensing electrodes are electrically connected a sensory controller of the device, wherein the sensor controller is linked to at least one sensor of the biological limb that detects application of at least one of position, velocity, acceleration, and force of the biological limb, and whereby the sensory controller transmits detection of the position, velocity, acceleration, and force of the biological limb to the motor controller, and whereby the motor controller applies electrical stimulation via the stimulating electrodes, thereby reversing impairments of the human limb.

In still another embodiment, the invention is directed to a method of restoring at least partial function of the human limb of an individual that includes dissecting at least one patch of skin from individual, translocating the patch of skin onto a non-anatomical portion of the individual, wherein the skin patch includes at least one nerve selected from the group consisting of an intact native nerve and a new regenerative innervation nerve, and contacting the translocated skin patch with an external device, the device including at least one component that provides mechanical stimulation to the translocated skin patch, thereby restoring at least partial function of the human limb.

In still another embodiment, the method of the invention includes reversing the impairment of an amputated limb, including inserting a distal end of at least one transected nerve of an amputated limb into a proximal end of a microchannel array, placing at least one member of the group consisting of skin and muscle end organ at the distal end of the microchannel array, thereby causing the nerve to regenerate through the microchannel array and to innervate the at least one end organ. Efferent motor information of the regenerated nerve is recorded using sensing electrodes within a plurality of afferent microchannels of the microchannel array. The regenerated nerve is stimulated with afferent sensory information using stimulating electrodes within a plurality of afferent microchannels of the microchannel array. The sensing electrodes are electrically connected to a motor controller of a device. The stimulating electrodes are electrically connected to a sensory controller of the device, wherein the motor controller is linked to at least one sensor of the device that detects application of at least one member selected from the group consisting of position, velocity, acceleration, and force of the device, and whereby the motor controller transmits detection of the position, velocity, acceleration, and force by applying electrical stimulation via the stimulating electrodes, thereby providing the individual with a sensation simulating sensory feedback from the device, and reversing impairment of the amputated limb.

In yet another embodiment of the invention, the method includes simulating proprioceptive sensory feedback from a device, including the steps of the mechanically linking at least one pair of agonist and antagonist muscles, wherein a nerve innervates each muscle. The at least one pair of agonist and antagonist muscles are supported with a support, whereby contraction of the agonist muscle of each pair will cause extension of the paired antagonist muscle. At least one electrode is implanted in at least one muscle of each pair, and the at least one electrode is electrically connected to a motor controller of the device, thereby stimulating proprioceptive sensory feedback from the device.

In another embodiment, the invention is a method for simulating cutaneous sensory feedback from the device, including steps of excising a skin segment from a biological body part of an individual, the skin segment including at least one of a native nerve and a regenerative nerve supply. The skin segment is linked to at least one muscle having a nerve supply. An electrode is implanted in the at least one muscle. The skin segment and actuator muscle are supported on a support. The at least one electrode is electrically connected to a sensory controller of a device, wherein the controller is linked to a sensor of the device that detects application of at least one of stress, strain, contact, pressure and sheer at the device, and whereby the controller transmits detection of the stress, strain, contact, pressure or sheer by contracting the actuator muscle within electrical stimulation via the electrode, thereby stretching the mechanoreceptor of the skin segment and providing the individual with a sensation stimulating cutaneous sensory feedback from the device.

This invention has many advantages. For example, Applicants' claimed invention provides a strategy for clinicians to follow when planning an amputation procedure so that the possibility to later obtain enhanced prosthetic control is maximized. Specifically, in the case of limb amputation, this strategy may include deriving multiple independent electrical signals, such as electromyographic signals, and neural recorded signals to command powered actuators within an external prosthesis. Further, artificial sensory information may be provided from the externally-controlled limb prosthesis back to the amputee by mechanically stimulating relocated cutaneous tissues salvaged from the amputated limb or, alternatively, bioelectrically activating sensory nerve fibers in the residual limb using a novel neural interface design.

The surgical reconstruction methodology and implantable system of the invention significantly increases the potential for natural neural control of prostheses, such as artificial limbs and functional electrical stimulation devices. The system utilizes the neural activity within the residual biological limb generated in the peripheral nerves and/or the electromyographic activity generated through muscle tissue activation. Such nerve and muscle tissues may be native to the residual limb, or they may be relocated to the residual limb through a plurality of surgical manipulations. Such manipulations may include free muscle grafts or pedicle muscle grafts, which may include intact attached nerves and/or vasculature. Additionally, the musculature could be derived from transplanted muscle precursor cells or cultured muscle tissue. For amputation limb patients, the system includes means to record one or multiple independent channels of neural motor activity that can control the various degrees of freedom present in advanced powered prosthetic limbs. Further, the method of the invention provides for the possibility of sensory information input from a controlled external prosthesis back into the nervous system. With regard to cutaneous sensory feedback, this can be by electrically activating sensory nerves through a nervecuff and/or microchannel array directly, or by applying mechanical stimulation to the native skin of the residual limb or other cutaneous tissue, such as fingertip skin, that has been relocated by a grafting procedure to the residual limb.

The invention also includes means to provide proprioceptive feedback to the amputee. This can be achieved through direct electrical activation of muscle and tendon afferent nerve fibers using the microchannel array. The invention also allows relocated antagonistic muscle pairs to mechanically interact with each other in a reciprocal push-pull fashion, just as would occur if the agonist/antagonist muscle pair were attached to the opposing sides of a joint. This approach allows the muscle proprioceptive endings that are intrinsic to those muscles to be activated by a normal stretch stimulus that occurs with intact muscles operating around the same joint.

The invention also has application in neural interface technology, such as for spinal cord lesion patients, stroke patients and other motor impairment disabilities, in that sensory information from the distal biological limb, or biological member, can be recorded from channels within an implanted microchannel array. Such signals can then be employed in an artificial feedback algorithm to then stimulate distal limb muscles through motor channels within the same microchannel array, or an alternate microchannel array.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 6A is a first representation of contacting a grafted patch of skin transplanted from finger pads of an individual with an external prosthetic socket of a prosthetic limb according to another method of the invention, wherein the prosthetic socket includes at least one actuator component that provides mechanical stimulation of the grafted patch of skin.

FIG. 6B is a second, subsequent representation of contacting a grafted patch of skin transplanted from finger pads of an individual with an external prosthetic socket of a prosthetic limb according to another method of the invention, wherein the prosthetic socket includes at least one actuator component that provides mechanical stimulation of the grafted patch of skin.

FIG. 6C is a schematic representation of a segment of the prosthetic and the actuator shown in FIG. 6B.

FIG. 6D is a schematic representation of the prosthetic of FIG. 6C after actuation of the actuator.

FIG. 7A is a schematic representation of contacting native sensory innervation of a skin patch with nerve cuffs, wherein the nerve cuffs are linked to a controller, and selectively stimulating the native sensory innervation by actuating the nerve cuffs with the controller, according to yet another embodiment of the invention.

FIG. 7B is another schematic representation of the embodiment of the invention shown in FIG. 7A, showing placement of implanted electronics and the nerve cuffs of FIG. 7A.

FIG. 8A is a schematic representation of transecting a nerve of a limb of an individual to thereby form proximal and distal ends of the transected nerve, and of placing the proximal and distal ends of the transected nerve in a microchannel array, the microchannel array including a bidirectional interface that records afferent information of the nerve and that provides efferent stimulus to the nerve, once the nerve has regenerated in the microchannel array, according to another embodiment of the method of the invention.

FIG. 8B is a representation of one embodiment of placement of the microchannel array at the surgical site of an individual and relative location of a prosthetic limb controlled by the microchannel array.

FIG. 13A is an exploded view of one embodiment of a three-dimensional microchannel array suitable for use by at least one method of the invention.

FIG. 13B is a perspective view of the assembled three-dimensional microchannel array of FIG. 13A.

DETAILED DESCRIPTION OF THE INVENTION

Figure 1:
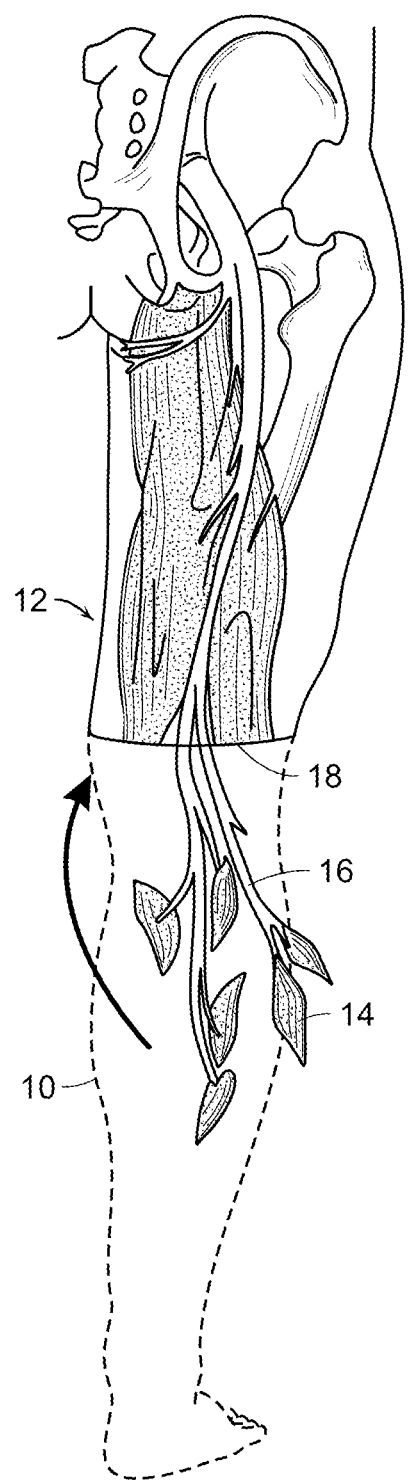
FIG. 1 is a schematic representation of surgical removal of a portion of an injured or diseased human limb, in outline, leaving intact a portion of selected muscles, including blood vessels and nerves associated with that portion of the selected muscles, according to one embodiment of the method of the invention.

A description of example embodiments of the invention follows.

The invention generally is directed to a method of restoring at least partial function of a human limb, to reversing motor impairment of a human limb, to simulating a proprioceptive sensory organ for a human limb or organ, and to simulating a cutaneous sensor organ for a human limb or organ of an individual.

One goal of amputation surgery is to use the muscle tissues at the distal end of the residual limb to provide an appropriate cone shape to the limb so that a prosthetist will be able to fit a socket to the limb that will receive an artificial prosthesis. The distal ends of amputated nerves are usually buried into fat tissue or deep into the residual limb to provide protection to them from mechanical stimulation, which might otherwise cause painful sensations.

One critical innovation that is described herein is a strategy for clinicians to follow when planning an amputation procedure so that the possibility to later obtain enhanced prosthetic control is maximized. In the case of limb amputation, this strategy would include deriving multiple independent EMG signals and neural recorded signals to command powered actuators within an external prosthesis. A further innovation is to provide for artificial sensory information from the external controlled limb prosthesis back to the amputee by mechanically stimulating relocated cutaneous tissues salvaged from the amputated limb, or by electrically activating sensory nerve fibers in the residual limb using a novel neural interface design.

EMG Acquisition Using Skin Surface Electrodes—

Myo-electric powered upper extremity prostheses have traditionally employed surface recording techniques to sense EMG activity. Typically, EMG signals are registered using small metal button-shaped electrodes that are mounted within the shell of the prosthesis socket so that they contact the skin overlying the muscles selected for the control tasks. Other electrode materials are possible, including conductive polymers, metal-impregnated woven fabrics, and carbon composites, for example.

To achieve an acceptable signal to noise ratio (SNR) and exclude unwanted biosignals, such as the electrocardiogram, a bi-polar recording configuration generally is recommended (C. J. De Luca, DelSys Inc. "Surface Electromyography: Detection and Recording," DelSys Inc., Tutorial, 2002), although other configurations, such as a tri-polar recording, configuration could be employed.

It is also possible to cover an area of skin with an array of electrode elements and combine their outputs in arbitrary combinations in order to improve the SNR or to improve the ability to isolate the activity of individual muscles. Surface EMG acquisition has the advantage that it is non-invasive and the electrodes can be relocated if desired. There are, however, several disadvantages associated with surface recording. These include low signal amplitudes and variability in the signal amplitude caused by perspiration, changes in the thickness of the subcutaneous fat between the electrode and the underlying muscle, and movement of the electrodes relative to the recorded muscle from rotation of the limb and stretching of the skin. Other serious limitations of surface recording are contamination of the signal from activity in neighboring muscles and the inability to record selectively from muscles that are not superficial.

EMG Acquisition Using Implanted Sensors—

The limitations imposed with surface recording of EMG activity can largely be mitigated by securing electrodes directly onto the epimesial surface of the muscle or by placing penetrating electrodes into the muscle tissue itself. Implantable epimesial electrodes and coiled wire intramuscular electrodes developed for electrical stimulation of muscle, but suitable for recording EMG activity, are known in the art. Variations of these designs could include bi-filar intramuscular coiled wire electrodes and epimesial electrodes, (P. A. Grandjean and J. T. Mortimer, "Recruitment properties of monopolar and bipolar epimysial electrodes," Annals of Biomedical Engineering, vol. 14, no. 1, pp. 53-66, 1986), which contain additional contact sites attached to a common backing.

An example of a suitable implantable device that acquires EMG activity from residual limb muscles for the control of powered artificial limbs is the BION2™ powered artificial limb, developed by the Alfred Mann Foundation which consists of a ceramic cylinder approximately 3 mm dia.×15 mm long that can be installed into a muscle by loading it into the lumen of a hypodermic needle and then withdrawing the needle, leaving the sensor behind in the tissue. Each sensor is a stand-alone device capable of recording electrical activity by means of electrode contacts that are located at the ends of the cylinder. Each sensor is addressable so that its registered data can be telemetered to a central receiver terminal located in the shell of the prosthesis. Power for the implanted sensors is supplied via an RF link from a single transmitter coil that is located around the circumference of the prosthesis shell and communicates with all of the BION2™ devices that are implanted in the tissues that lie beneath the coiled region. An example application of these sensors is in an Implantable Myoelectric Sensor (IMES) System, described in R. F. Weir, P. R. Troyk, G. A. DeMichele, D. A. Kerns, J. F. Schorsch, and H. Maas, "Implantable myoelectric sensors (IMESs) for intramuscular electromyogram recording," IEEE Transactions on Biomedical Engineering, vol. 56, no. 1, pp. 159-171, 2009.

Another implementation of an implantable EMG controller system includes a centralized processer package that resembles a "pacemaker" module. It has several paired leads that extend from the processor out to individual muscles. Each set of leads terminates in a set of button-shaped electrodes that are sutured to the epimesium of the muscles used to control the actuators of a powered prosthesis. More recently, a smaller device has been developed that includes an ASIC dedicated specifically for recording and transmitting EMG activity. (B. D. Farnsworth, Wireless Implantable EMG Sensing Microsystem, Masters thesis, Case Western Reserve University, August 2010).

Direct Interfacing to Peripheral Nerves—

It has long been recognized that superior prosthetic limb control could be obtained if it was possible to establish the means to achieve a bi-directional interface with the peripheral nerves present in the residual limb. Researchers have applied several different approaches to achieve this goal, (K. Yashida and R. Riso, "Peripheral nerve recording electrodes and techniques," in Neuroprostheses in Theory and Practice vol. 2, K. W. Horch and G. S. Dhillon, Eds. Hakensack, N.J.: World Scientific, 2004, pp. 683-744), including various designs of circumferential nerve cuffs (e.g., Huntington Helix, W. F. Agnew, D. B. McCreery, T. G. H. Yuen, and L. A. Bullara, "Histologic and physiologic evaluation of electrically stimulated peripheral nerve: Considerations for the selection of parameters," Annals of Biomedical Engineering, vol. 17, pp. 39-60, 1989); self sizing spiral cuffs (G. G. Naples, J. T. Mortimer, A. Scheiner, and J. D. Sweeney, "A spiral nerve cuff electrode for peripheral nerve stimulation," IEEE Transactions on Biomedical Engineering, vol. 35, no. 11, pp. 905-916, 1988); multi-polar cuffs (C. Veraart, W. M. Grill, and J. T. Mortimer, "Selective control of muscle activation with a multipolar nerve cuff electrode," IEEE Transactions on Biomedical Engineering, vol. 40, no. 7, pp. 640-653, 1993; M. Schuettler and T. Stieglitz, "18polar hybrid cuff electrodes for stimulation of peripheral nerves," in Proceedings of the International Functional Electrical Stimulation Society, Aalborg, Denmark, pp. 265-268, 2000) and cuffs with multiple chambers, (J. A. Hoffer, Y. Chen, K. Strange, and P. R. Christensen, "Nerve cuff having one or more isolated chambers," U.S. Pat. No. 5,824,027 A, Oct. 20, 1998). Such "wrap around" cuffs designs have the inherent limitation that it is difficult to record from or to stimulate nerve fascicles that are not located on the surface of the nerve and that may lie deep within the trunk nerve. One cuff design acts to mitigate this problem by flattening and hence reshaping the nerve to force fascicles to align side by side, thereby providing more equal access to all fascicles of the nerve, (D. Tyler and D. Durand, "Flat interface nerve electrode and a method for use," U.S. Pat. No. 6,456,866 B1, Sep. 24, 2002).

Penetrating Interfascicular Electrodes and Micro-Electrode Arrays—

Efforts to achieve better fiber specificity for recording and stimulation have led to the development of an array of needle-like electrodes (resembling a brush) having 100 contact points that is inserted transversely into the peripheral nerve. This approach allows nearly single unit specificity, similar to what is achieved using individual micro-electrodes. Despite this inherent advantage, thus far, electrode stability remains a major issue, because the electrode contact points tend to be extruded away from their original nerve fiber locations over time, (A. Branner and R. A. Normann, "A multielectrode array for intrafascicular recording and stimulation in sciatic nerve of cats," Brain Research Bulletin, vol. 51, no. 4, pp. 293-306, 2000).

Another strategy to achieve high fiber specificity involves drawing fine wire or conductive polymer filaments into the nerve, essentially using a sewing technique for implantation. Each filament contains a small zone that is an electrode contact site and is capable of recording or stimulating nearby nerve fibers. Again, while this approach has shown the ability to isolate individual nerve fiber activity, over time the contact site moves relative to the nerve fibers, so that long term stability so far typically is not adequate for clinical use (M. S. Malagodi, K. W. Horch, and A. A. Schoenberg, "An intrafascicular electrode for recording of action potentials in peripheral nerves," Annals of Biomedical Engineering, vol. 17, pp. 397-410, 1989; K. Yoshida and R. B. Stein, "Characterization of signals and noise rejection with bipolar longitudinal intrafascicular electrodes," IEEE Transactions on Biomedical Engineering, vol. 46, no. 2, pp. 226-234, 1999; and S. M. Lawrence, J. O. Larsen, K. W. Horch, R. Riso, and T. Sinkjaer, "Long-term biocompatibility of implanted polymer-based intrafascicular electrodes," Journal of Biomedical Materials Research, vol. 63, no. 5, pp. 501-506, 2002). Another severe limitation is that the number of fibers that can be "sewn" into a given nerve is very small (~perhaps 10), and this can result in a very poor sampling of the potential information that is available in a peripheral nerve.

Regeneration-Based Nerve Interfaces—

Regardless of advances made in cuff-based nerve interface designs, the extent of specificity that can be obtained for stimulating and recording is still extremely limited. Much better selectivity can be achieved if the fibers at the end of an amputated nerve are allowed to grow into a structure that consists of an array of micro-channels. Experience has shown that nerve fibers will invade each of the channels, and this effectively separates the nerve into small numbers of fibers that are likely to share some commonalities in function. Thus, a single micro-channel can include motor fibers that originally subserved a single muscle rather than multiple muscles. Similar benefits apply with regard to sensory nerve fibers, where the contents of a single micro-channel can include of sensory fibers that are of a single sensory modality, such as light touch or sustained pressure, or fibers that have receptive fields restricted to a small perceived locus on the phantom limb.

The development of regeneration electrodes began with "sieve" type designs that were disks with an array of fine caliber holes or slots drilled through them, (see, e.g., D. J. Edell, "A peripheral nerve information transducer for amputees: long-term multichannel recordings from rabbit peripheral nerves," IEEE Transactions on Biomedical Engineering, vol. 33, no. 2, pp. 203-214, 1986; G. T. A. Kovacs, C. W. Storment, and J. M. Rosen, "Regeneration microelectrode array for peripheral nerve recording and stimulation," IEEE Transactions on Biomedical Engineering, vol. 39, no. 9, pp. 893-902, 1992; R. M. Bradley, R. H. Smoke, T. Akin, and K. Najafi, "Functional regeneration of glossopharyngeal nerve through micromachined sieve electrode arrays," Brain Research, vol. 594, no. 1, pp. 84-90, 1992; R. M. Bradley, X. Cao, T. Akin, and K. Najafi, "Long term chronic recordings from peripheral sensory fibers using a sieve electrode array," Journal of Neuroscience Methods, vol. 73, no. 2, pp. 177-186, 1997; T. Akin, K. Najafi, R. H. Smoke, and R. M. Bradley, "A micromachined silicon sieve electrode for nerve regeneration applications," IEEE Transactions on Biomedical Engineering, vol. 41, no. 4, pp. 305-313, 1994; Navarro, S. Calvet, F. J. Rodriguez, T. Stieglitz, C. Blau, M. Buti, E. Valderrama, and J. U. Meyer, "Stimulation and recording from regenerated peripheral nerves through polyimide sieve electrodes," Journal of the Peripheral Nervous System, vol. 3, no. 2, pp. 91-101, 1998; L. Wallman, Y. Zhang, T. Laurell, and N. Danielsen, "The geometric design of micromachined silicon sieve electrodes influences functional nerve regeneration," Biomaterials, vol. 22, no. 10, pp. 1187-93, 2001; and L. Wallman, A. Levinsson, J. Schouenborg, H. Holmberg, L. Montelius, N. Danielsen, and T. Laurell, "Perforated silicon nerve chips with doped registration electrodes: in vitro performance and in vivo operation," IEEE Transactions on Biomedical Engineering, vol. 46, no. 9, pp. 1065-73, 1999). Such designs generally did not perform well because the electrode faces were located on the flat surfaces of the disks (perpendicular to the direction of nerve growth) and because the sharp edges of the holes could cut the nerve fibers that grew through the device. A more satisfactory design was a disk that was thick enough so that the electrode faces could be placed within lengthened holes, referred to as micro-channels. An example of early implementation of a micro-channel approach was in the MIT Biomechatronics Research Group, in collaboration with InnerSea Technology, where a bundle of 200 um ID polyimide tubing was sheared to a length of 3 mm to form a micro-channel array. Sharpened metal microelectrodes were introduced into the lumen of some of the channels so that neural recordings could be performed. The tibial nerve in a rabbit model was transected, and then the proximal nerve stump was allowed to grow into the implanted micro-channel array to form a reconnection to the distal nerve stump in a nerve-to-nerve repair. After recovery, it was demonstrated that neural activity could be recorded from the various array channels, and subsequent histological studies showed that the majority of the array channels contained regenerated nerve fibers and supporting vasculature (D. Edell, R. Riso, and H. Herr, "Bi-directional peripheral nerve interface for the control of powered prosthetic limbs," DARPA Contract N66001-05-C-8030, 2006). Furthermore, in separate experiments using a "Y" maze paradigm, in which regenerating fibers were given a choice of growing into one of two chambers containing a small slice of either skin tissue or muscle tissue, it was shown that such "target tissues" are useful in trying to achieve a separation of motor efferent nerve fibers from sensory cutaneous afferent nerve fibers (D. Edell et al.). These studies were subsequently referenced as the basis for a patent submission that describes nerve regeneration based nerve interfacing (D. J. Edell and R. R. Riso, "Long term bi-directional axon-electronic communication system," U.S. patent application Ser. No. 11/629,257, filed on Jun. 15, 2005 and published on Sep. 18, 2008 as U.S. 2008/0228240).

Subsequent developments of the micro-channel nerve interface strategy using a rat amputated nerve model in other laboratories (J. J. Fitzgerald, S. P. Lacour, S. B. McMahon, and J. W. Fawcett, "Microchannels as axonal amplifiers," IEEE Transactions on Biomedical Engineering, vol. 55, no. 3, pp. 1136-1146, 2008; J. J. Fitzgerald, N. Lago, S. Benmerah, J. Serra, C. P. Watling, R. E. Cameron, E. Tarte, S. P. Lacour, S. B. McMahon, and J. W. Fawcett, "A regenerative microchannel neural interface for recording from and stimulating peripheral axons in vivo," Journal of Neural Engineering, vol. 9, no. 1, pp. 016010, 2012; and S. P. Lacour, J. J. Fitzgerald, N. Lago, E. Tarte, S. McMahon, and J. Fawcett, "Long micro-channel electrode arrays: a novel type of regenerative peripheral nerve interface," IEEE Transactions on Neural Systems and Rehabilitation Engineering, vol. 17, no. 5, pp. 454-60, 2009) have corroborated the hypothesis that a transected nerve will regenerate into a micro-channel structure and that electrodes placed within individual channels can record neural activity with minimal cross-talk (signal leakage) between channels.

First Embodiment

Description of Specific Embodiments of the Invention

Figure 2A:
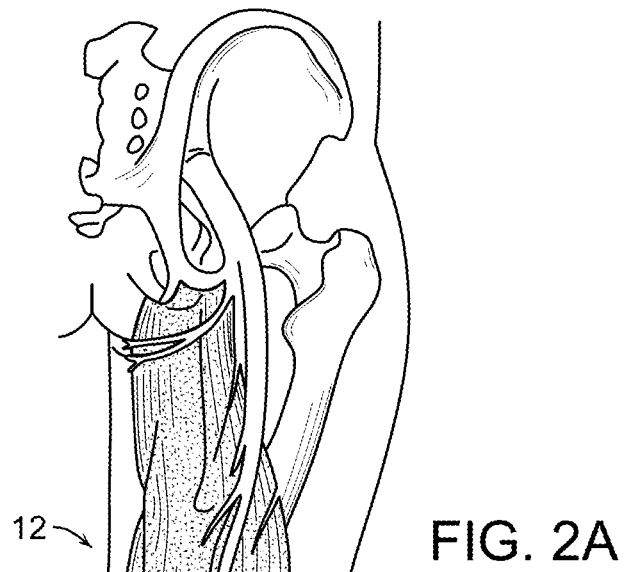
FIG. 2A is a schematic representation of transplantation of the selected muscles of FIG. 1 to a surgical site of the individual where the limb was removed according to the embodiment of the method of the invention of FIG. 1.
Figure 2B:
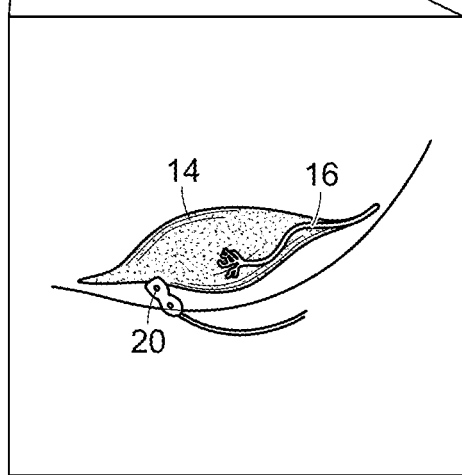
FIG. 2B is a schematic representation of implanting an electrode on to the epimesial surface of the selected muscles of FIG. 2A.

FIGS. 1, 2A and 2B are schematic representations of one embodiment of the method of the invention that includes the method of the restoring at least partial function of a human limb. At least a portion 10 (shown in outline) of an injured or diseased human limb 12 from an individual is surgically removed, leaving intact at least a portion of selected muscles 14 from the damaged portion of the human limb, including blood vessels and nerves 16 associated with that portion of the selected muscles 14. The selected muscles are transplanted to a surgical site 18 of the individual where the human limb was removed. The transplanted selected muscles 14 and associated nerves 16 are then contacted with electrodes 20 (FIGS. 2A and 2B), whereby signals can be transmitted to and from nerves 16 at the transplanted muscles 14 to thereby control a prosthetic limb (not shown) that is linked to the electrodes and extends from the surgical site 18.

A model for a transfemoral (above-the-knee) amputation is illustrated in FIG. 1, but it will be clear to those of ordinary skill in the art that this embodiment is more broadly applicable to any amputation surgery in which muscles from the distal (amputated) limb can be salvaged with their native nerve innervation intact and perhaps, when possible, their native vasculature. For example, this embodiment could be applied to transhumeral, transradial, and transtibial amputation procedures. In such procedures, muscles can be relocated to the portion of the limb that is retained after the amputation surgery, providing new sources of signals, such as EMG signals, that can be harnessed for the control of advanced external devices, such as limb prostheses, orthoses or exoskeletons.

In a specific embodiment, using surface recording techniques, EMG signals from both the native and re-located muscles are sensed from electrodes mounted in the prosthetic socket shell, where electrodes contact the skin overlying the targeted muscles. Alternatively, an IMES implantable sensor, such as discussed earlier, is employed to measure and transmit the EMG signal from both native and re-located muscles within the residual biological limb post amputation surgery.

Listed below are examples of muscles that can be transferred to the residual limb during a transfemoral amputation surgical procedure in order to gain signals for the ankle and subtalar joint control of a prosthesis:

Tibialis anterior m.—ankle dorsiflexion and eversion
Gastronemius m.—ankle plantar flexion
Soleus m.—ankle plantar flexion
Posterior tibialis m.—ankle inversion
Peroneus Longus—eversion and plantar flexion of ankle Additionally, this embodiment of the invention can be employed to control actuation of toes. This can be achieved by employing EMG command signals recorded from, for example, the following leg muscles:

Flexor Digitorum longus—$2^{nd}$ toe flexor
Extensor Digitorum longus—$2^{nd}$ toe extensor
Flexor Hallucis longus—great toe flexor
Extensor Hallucis longus—great toe extensor In the case of a transfemoral amputation, surface recording electrodes can be employed to register the activity of the residual limb's native knee flexor and extensor muscles, such as the quadriceps and hamstring muscle groups, for the control of prosthetic knee extension and flexion, respectively. The knee joint is fundamentally a single degree of freedom joint and can be controlled using a single flexor and extensor muscle pair. Preferably, EMG command signal contributions from as many of the knee-controlling muscles as possible can be obtained so that the impedance (stiffness and damping) of the knee joint in an advanced prostheses can be accurately modulated during ambulation and other lower-extremity activities.

During surgery, viable muscles and their native innervation in the portion of the limb that will ultimately be amputated are dissected and packed into the residual limb, as shown in FIGS. 2A and 2B. Nerves to a target muscle can be mobilized by interfasicular dissection where possible or by freeing the entire trunk nerve and removing extraneous branches to muscles that will not be re-located and used for prosthesis control.

Figure 3:
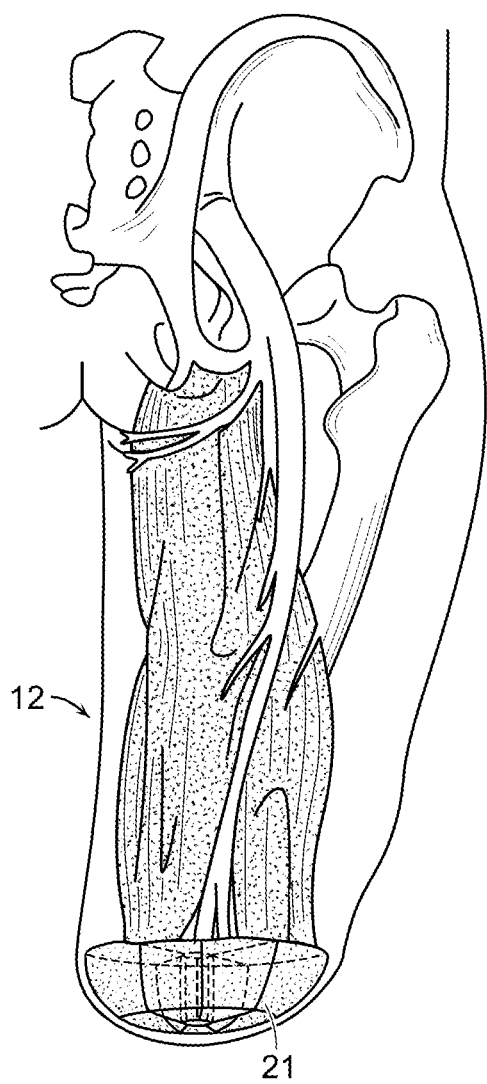
FIG. 3 is a schematic representation of providing electrical isolation between relocated and native muscles.

Depending on the positioning of the native and relocated muscles relative to each other, it may be necessary to provide means to electrically isolate some or all of the muscles to prevent electrical cross talk between the recording channels. Electrically isolating native muscle tissue has previously been discussed by Kuiken, who suggested using fat tissue or silicone sheeting to wrap portions of the native muscles and thus prevent the spread of objectionable action currents between native muscles, (T. Kuiken, N. Stoykov, M. Lowery, and A. Taflove, "Finite element analysis of EMG signals to improve the control of myoelectric prostheses," in 10th World Conference of the International Society for Prosthetics and Orthotics, Glasgow, U K, 2001). Silicone is an acceptable material for this purpose because it is highly biocompatible, easily molded into arbitrary shapes, and possesses a high dielectric constant. One possible scheme of providing electrical isolation between relocated and native muscles in the residual limb is depicted in FIG. 3. During surgery, relocated muscles can be packed into a multi-chamber silicone structure 21, which can be held in place by sutures to tissues or by attachment to bone in the residual limb. Such a structure can also help in preventing residual limb pain by padding the end of the residual bone, for example, and by mechanically shielding relocated nerve fibers from forces exerted to the exterior surfaces of the residual limb. Other materials or combinations of materials, such as laminated structures, can be employed as well. This technique can be particularly beneficial if specific stiffness properties are desired to reconstruct the residual limb to better accommodate the forces exerted against the tissues by the external prosthetic socket.

After surgery, EMG signals from the relocated muscles and any relevant native residual limb muscles are sensed with surface electrodes mounted in the prosthesis socket so that the electrodes contact the skin overlying the targeted muscles. These electrodes can also be mounted directly on the skin. Alternatively, implanted sensors such as the IMES described previously could be employed to acquire the EMG control signals from native and relocated muscles.

The method of the invention described with reference to FIGS. 1, 2A and 2B typically requires no nerve transection, or grafting, though such additions can be made if the amputation demands it (e.g. a small portion of the nerve to a target muscle is damaged).

Second Embodiment

Figure 4:
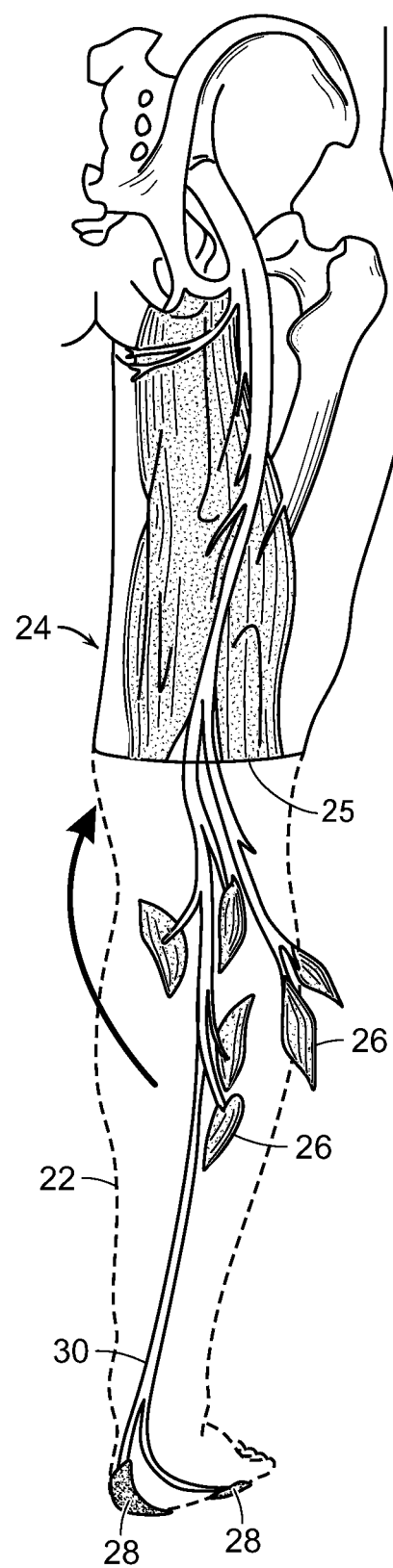
FIG. 4 is a schematic representation of surgical removal of a portion of an injured or diseased human limb, in outline, leaving intact a portion of selected muscles and selected glabrous skin patches, including blood vessels and nerves associated with those portions of the selected muscles and glabrous skin patches, according to another embodiment of the invention.
Figures 5A, 5B:
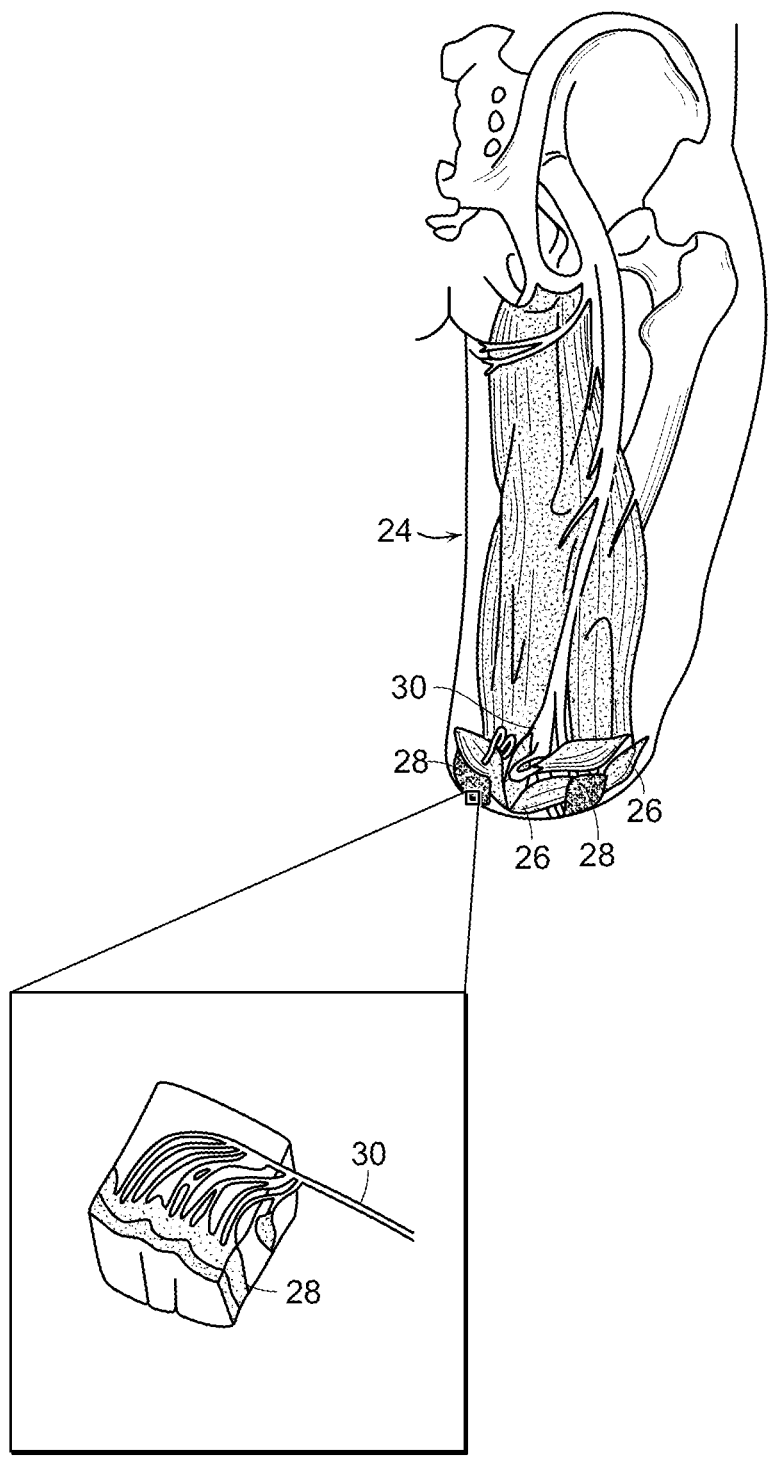
FIG. 5A is a schematic representation of grafting a patch of skin into the individual shown in FIG. 4 at the surgical site where the limb or limb portion was removed according to the embodiment of the invention of FIG. 4.
FIG. 5B is a cross section of the patch of skin grafted into the individual as shown in FIG. 5A.

FIGS. 4-6D are schematic representations of a second embodiment of a method of the invention for restoring at least partial function of a human limb. Specifically, FIG. 4 is a schematic representation of surgical removal of a portion 22 (in outline) of an injured or diseased human limb 24, in outline, leaving intact a portion of selected muscles 26 and selected glabrous skin patches 28, including blood vessels and nerves 30 associated with those portions of the selected muscles 26 and glabrous skin patches 28, according to another embodiment of the invention. Alternatively, or in addition, the nerve can be a new regenerative innervation nerve. "New regenerative innervation nerve," as that term is employed herein, is a nerve that has regenerated or grown into muscle or skin cells. Similarly, an "end organ," as that term is employed herein, is a tissue body into which a nerve regenerates. Thus, a muscle body or a skin body into which a nerve has regenerated are end organs. FIG. 5A is a schematic representation of grafting a patch of skin 28 into the individual shown in FIG. 4 at the surgical site 25 where the limb or limb portion was removed according to the embodiment of the invention of FIG. 4. FIG. 5B is a cross section of the patch of skin 28 grafted into the individual as shown in FIG. 5A.

As represented in FIGS. 4-6D, a transfemoral amputation is again shown, but, as with the embodiment represented in FIGS. 1-3, it should be understood that this surgical model is applicable to any amputation with viable tissues in the amputated limb. This embodiment includes muscle relocation and recording, such as an EMG recording, as described above with respect to the embodiment represented in FIGS. 1-3.

This second embodiment, however, provides for cutaneous sensory input by dissecting relevant patches of skin from the amputated portion of the limb together with the native innervation or new regenerative innervation, and then grafting these skin patches onto a non-anatomical portion of the individual from whom the limb was removed. A "non-anatomical portion of an individual," as that term is employed herein, means a tissue location that is not a natural anatomical location for that tissue. For example, if a foot muscle is translocated up the leg to the thigh, it can be stated that the muscle was inserted into a non-anatomical portion of the individual. The skin patches can be taken, for example, from a hand or foot of an individual. For a lower extremity amputation, these skin patches would be taken, for example, from the heel, forefoot sole, and/or toe pads. One or more mechanical devices can then be mounted in the walls of the external prosthetic socket to provide mechanical stimulation to the grafted skin areas. Such stimulation can be driven according to an array of appropriately located sensors covering the external prosthetic limb. In the case of a lower-extremity prosthesis, the system can include pressure distribution normal to the foot areas and shear forces in the anterior-posterior and medial-lateral directions. Advanced implementation of this strategy may also provide information about slippage events and possibly frictional and textural features between the ground and the shoe sole. Because the topographic mapping of the foot skin to the brain is largely preserved following the amputation, any stimulation of the transferred skin areas will evoke tactile sensations that are referred to the foot. This same strategy can also include relocating slips of skin from the dorsum of the forefoot, which can provide useful feedback for an amputee kicking a soccer ball, for example. Using synthetic external pressure and shear sensing on the prosthetic foot, a microprocessor or processors can then send out control commands to small actuators imbedded within the socket interface to apply equivalent pressures and shear stresses onto the corresponding relocated skin tissues surrounding the residual limb. For example, when the bionic limb's heel strikes the ground surface during a walking gait cycle, small actuators imbedded within the residual socket wall may apply proportional forces to the relocated heel skin patch located on the residual limb surface.

In similar fashion, upper extremity amputees can benefit from feedback of tactile events during object grasping and manipulation tasks. As illustrated in FIGS. 6A-6D, skin patches 32 and their native innervation from the finger tips 34 and thumb 35 and selected locations from the palm 36 may be relocated to the residual limb 38, where they can be mechanically stimulated by actuators 40 contained within a socket shell 42 of an external prosthesis, as shown in the transition from FIG. 6C to FIG. 6D. For example, under neural control, a bionic upper extremity prosthesis can be controlled to grip the outside surface of a glass of water. Pressure and shear sensory information recorded within the palm 36 and finger tips 34 of the prosthetic hand may be received by a microprocessor or microprocessors located on the external prosthesis. The computer(s) can conduct computations and in turn provide control commands to actuators within the prosthetic socket wall 44 (See FIGS. 6C and 6D) where commensurate pressures and shear forces may be applied to the corresponding skin patches 32, e.g., pressure $P_0$ measured on the forefinger tip of the bionic hand may be applied to the forefinger skin patch located on the residual limb surface. Such afferent feedback into the human nervous system may then inform descending efferent motor commands that are recorded as EMG signals from the native and relocated muscles, which in turn, may then be used to control the actuators within the external bionic hand to effectively modulate its gripping force. The actuators within the socket wall 44 shown in FIGS. 6C and 6D that exert forces on the relocated cutaneous tissues for afferent feedback can be selected from a number of different actuator types, including but not limited to pneumatic bladders, electroactive polymer (EAP) artificial muscle, and electric motor with a ballscrew transmission.

Another embodiment of the present invention is to denervate a portion of the native skin of the residual limb during the amputation surgery, and graft cutaneous transected nerve stumps directly to the denervated skin region. In this framework, the cutaneous nerve axons at the residual-limb level that once innervated skin sections of the distal amputated limb are grafted directly to the native skin in the area of the residual limb. By this action, skin patches need not be re-located from the distal limb, but rather the native skin of the residual limb can be exploited for afferent feedback of force, pressure and/or shear signals measured using synthetic sensors located on the external prosthesis, and in turn, applied to the appropriate residual-limb skin patch using socket actuators. It should be noted that the location of cutaneous afferent skin patches, and the corresponding socket actuators, may be carefully selected so as not to include skin areas that are required to support high socket loads during afferent feedback periods. For example, the most distal aspect of the residual limb of lower extremity amputee patients does not typically take high socket pressures during standing and walking, and thus such a region may be ideal for afferent feedback.

Therefore, in specific applications of this second embodiment, for example, at least one flap of glabrous skin is dissected to thereby remove a patch of the skin from the limb, leaving intact the native sensory innervation of the skin patch, followed by grafting the patch of skin onto the individual at the surgical site where the limb or limb portion was removed. The grafted skin patch is contacted with an external prosthetic socket for the prosthetic limb. The prosthetic socket includes at least one component providing mechanical stimulation to the grafted skin. Examples of patches of skin include at least one member selected from the group consisting of a thumb, finger, palm, heel, four foot sole, and toe pad of the individual. Preferably, the component of the prosthetic socket applies pressure to a grafted patch of skin.

Third Embodiment

A third embodiment of the method of restoring at least partial function of a human limb of the invention includes sensory feedback and, as illustrated in FIGS. 7A-7B, the use of implanted electrodes 46 at muscles 48 and other implanted electronics 55 for registering EMG activity. FIG. 7A is a schematic representation of contacting native sensory innervation 50 of a skin patch 52 with nerve cuffs 54, wherein the nerve cuffs 54 are linked to a controller 56, and selectively stimulates native sensory innervation by actuating the nerve cuffs 54 with the controller 56. Nerve cuffs 54 are linked to implanted electronics 55 which are, in turn connected, such as by a wireless connection, to controller 56, as shown in FIG. 7A. FIG. 7B is another schematic representation of the embodiment of the invention shown in FIG. 7A, showing placement of implanted electronics and the nerve cuffs of FIG. 7A. In this embodiment, relocated distal skin 52 and its native sensory nerves 50 are packaged inside the residual limb 58 during amputation surgery. Sensory information is provided by electrically stimulating the sensory nerves using nerve cuffs 54 directly wrapped around the nerves 50.

Nerve cuff technologies generally do not possess sufficient selectivity to be able to activate specific modalities of tactile afferents. This limits the qualities of the evoked sensory experiences to isolated tapping events (for single pulse stimuli) or vibratory sensations if trains of pulses are delivered. Moreover, because of these deficiencies of selectivity, known nerve cuff technologies typically do not discriminate well between motor and sensory fibers. Thus, nerve cuffs intended to provide sensory feedback might only be applied to pure sensory nerves. For the case of mixed nerves, motor and sensory fascicles should not be stimulated simultaneously to avoid evoking undesirable contractions in muscles innervated by the mixed nerves that would contribute to undesirable background signal activity, such as EMG signal activity, in the residual limb (this complication would not arise if following the amputation surgery, the motor fibers of a mixed nerve no longer possess connections to muscle tissue, however).

For the lower extremity, examples of targeted pure sensory nerves include the sural and saphenous nerves. Well-localized tactile information from the footsole and toes could come from cutaneous fascicles of the tibial and peroneal nerves. However, because these nerves comprise mixed motor and sensory fibers, a neural interface that is more selective than nerve cuffs would be required to ensure that only the desired sensory nerve fibers are electrically stimulated. For upper extremity applications, the distal median, ulnar, and radial nerve cutaneous fascicles of the hand and fingers could be instrumented to provide cutaneous sensory feedback.

Regarding prosthesis motor control, as was the case in embodiments of the invention represented in FIGS. 1-6D and associated text, muscles from the amputated limb are relocated with their native innervation to the residual limb. However, whereas previous embodiments sometimes relied on surface electrodes to record EMG signals, this third embodiment employs implanted electrodes. More specifically, motor commands for the prosthesis can be derived from EMG signals recorded using electrodes implanted on the epimesium of targeted muscles or using intramuscular electrodes. It is also possible to use other EMG sensing strategies, such as mesh arrays containing electrode sites that feature embedded, distributed electronics for amplification and signal acquisition, (B. Tian, J. Liu, T. Dvir, L. Jin, J. H. Tsui, Q. Qing, Z. Suo, R. Langer, D. S. Kohane, and C. M. Lieber, "Macroporous nanowire nanoelectronic scaffolds for synthetic tissues," Nature Materials, vol. 11, pp. 986-994, 2012; and D.-H. Kim, N. Lu, R. Ghaffari, Y.-S. Kim, S. P. Lee, L. Xu, J. Wu, R.-H. Kim, J. Song, Z. Liu, J. Viventi, B. de Graff, B. Elolampi, M. Mansour, M. J. Slepian, S. Hwang, J. D. Moss, S.-M. Won, Y. Huang, B. Litt, and J. A. Rogers, "Materials for multifunctional balloon catheters with capabilities in cardiac electrophysiological mapping and ablation therapy," Nature Materials, vol. 10, pp. 316-323, 2011).

This third embodiment also employs wirelessly powered and controlled implanted electronics module to provide electrical stimuli to relocated sensory nerves and to acquire EMG activity from epimesial and/or intramuscular electrodes on relocated muscles.

A similar system can be applied in cases when target skin on an amputated limb cannot be mobilized and relocated while leaving its native innervation intact along the entire distance from the hand or foot sole to the residual limb. In such cases, relevant glabrous skin from the amputated limb is first isolated, leaving a short segment of its native nerve attached if possible. This tissue is then implanted into the residual limb, and a nerve-to-nerve repair is performed to connect the individual glabrous skin samples to appropriate sensory fascicles from amputated trunk nerves in the residual limb. The manner of nerve repair may be end-to-end, end-to-side, or a combination of these. If the skin is transferred without its innervation, appropriate nerves in the residual limb are grafted directly to the transferred grafted skin. Nerve cuffs can then be employed as previously described to the repaired nerve for sensory stimulation.

In a closed-loop paradigm between a human and a wearable device, sensory information recorded using synthetic sensors on the external device and/or human is mapped to appropriate afferent signals using microprocessor(s) located on the wearable device. After this computational step, stimulation commands are sent wirelessly to the implanted electronics which causes electrical stimulations through the nerve cuffs. The character and magnitude of these nerve stimulations will vary depending on the type of sensory feedback and the strength of that feedback. Such afferent signaling enables the human wearer to better modulate descending motor efferent signals that are recorded using the implanted muscle electrodes for sensing EMG activity. Such muscle signals are communicated wirelessly by the implanted electronics to the external prosthetic microprocessor(s) that then control motor(s) to drive the prosthesis.

Therefore, in this third embodiment, native sensory innervated skin patches are contacted with the nerve cuff that is linked to a controller and the native sensory innervation is selectively stimulated by actuating a nerve cuff with the controller. In another embodiment, the native sensory innervation includes at least one sensory neuron selected from the group consisting of sural, saphenous, tibial, peroneal, distal median, ulnar and radial nerves. In still another embodiment, the nerves of the transplanted selected muscles are contacted with electrodes that are implanted on the epimesium of the selected muscles, or implanted intramuscularly in the selected muscles. In another embodiment, the transplanted muscles are contacted with at least one mesh array that includes electrodes having embedded, distributed electronics that selectively detect and amplify detected signals from the transplanted muscles. In yet another embodiment, signals are detected from at least one transplanted muscle and are employed to modulate signals transmitted by the controller to the native sensory innervation of the at least one skin patch. Another embodiment further includes the step of establishing a nerve-to-nerve connection and communication between at least one severed nerve of the transplanted skin patch and a remaining native nerve of the individual. In another embodiment, the connection is between ends of the respective nerves, between the end of one nerve and a side of the other nerve, or a combination of both types of connections. In one specific embodiment, the electrode at the transplanted muscle and at the nerve cuff of the grafted skin patch are linked to the controller by a wireless connection. The connection between the severed nerve of the transplanted skin patch and the remaining native nerve of the individual can be bidirectional. Yet another embodiment further includes the step of co-locating the nerve of the transplanted selected muscle with the connection between the severed nerve of the transplanted skin patch and the remaining native nerve of the individual to form a neural interface. For example, the neural interface can include a microchannel array having a proximal end and a distal end, wherein at least one native nerve extends from the proximal side of the microchannel array and nerves of the transplanted muscle and skin graft extend from the distal side of the microchannel array. One specific such embodiment further includes the step of partitioning, at the neural interface, at least one nerve associated with the transplanted muscle from at least one nerve associated with the skin graft. The method can further include the step of regenerating the transplanted muscle nerve and the skin graft nerve by co-locating the transplanted muscle nerve and the skin graft nerve with respective proximal native nerves at the neural interface according to their respective functions. In one specific such embodiment, the neural interface includes at least one chemotrophic substance partitioned by the distribution of nerves within the neural interface. The neural interface can include at least one immunosuppressant. The method of the invention can further include the step of mapping external sensors of the prosthesis to afferent signals received from at least one of the transplanted muscles and the skin grafts, whereby the controller modulates, at least in part, efferent signals to at least one of the transplanted muscles and the prosthesis, to thereby at least assist the individual in manipulating the prosthesis. Still another embodiment further includes the step of selectively activating nerves at the neural interface. Another embodiment of the method of the invention further includes the step of recording signals communicated by nerves at the neural interface.

Fourth Embodiment

A fourth embodiment of the invention is a method of reversing motor impairment of a human limb and is intended to treat the situation where sufficient viable muscles are not available to provide adequate command signals, such as EMG command signals. Instead, this embodiment utilizes one or more bi-directional neural interface devices to record efferent motor nerve activity for external prosthetic control and to allow for sensory nerve stimulation triggered by signals from artificial sensors mounted externally on the prosthesis and/or user's body. In this embodiment, the invention is a method of reversing motor impairment of the human limb including transecting a nerve associated with reduced motor control of a limb of an individual to thereby form proximal and distal ends of the transected nerve. The proximal and distal ends of the transected nerve are placed in a micro channel array that includes a bidirectional interface that records sensory afferent information of the nerve and that provides efferent motor stimulus to the nerve once the nerve has regenerated in the micro channel array.

In this embodiment, the method of reversing impairment of a human limb can include transecting a nerve associated with the impairment of the limb of an individual to thereby form proximal and distal ends of the transected nerve. The proximal and distal ends of the transected nerve are placed into proximal and distal ends of a microchannel array, thereby causing the nerve to regenerate through the microchannel array. Sensory afferent information of the regenerated nerve is recorded using sensing electrodes within a plurality of afferent microchannels of the microchannel array. Motor efference information is stimulated to provide efferent motor stimulus to the nerve using stimulating electrodes within the plurality of efferent microchannels of the microchannel array. The stimulating electrodes are electrically connected to a motor controller of a device. A "device," as that term is employed herein, can refer, for example, to a prosthetic, orthotic or exoskeletal device. The sensing electrodes are electrically connected a sensory controller of the device, wherein the sensor controller is linked to at least one sensor of the biological limb that detects application of at least one of position, velocity, acceleration, and force of the biological limb, and whereby the sensory controller transmits detection of the position, velocity, acceleration, and force of the biological limb to the motor controller, and whereby the motor controller applies electrical stimulation via the stimulating electrodes, thereby reversing impairments of the human limb.

In another example of the fourth embodiment, the invention is directed to a method of restoring at least partial function of the human limb of an individual that includes dissecting at least one patch of skin from individual, translocating the patch of skin onto a non-anatomical portion of the individual, wherein the skin patch includes at least one nerve selected from the group consisting of an intact native nerve and a new regenerative innervation nerve, and contacting the translocated skin patch with an external device, the device including at least one component that provides mechanical stimulation to the translocated skin patch, thereby restoring at least partial function of the human limb.

Figure 9:
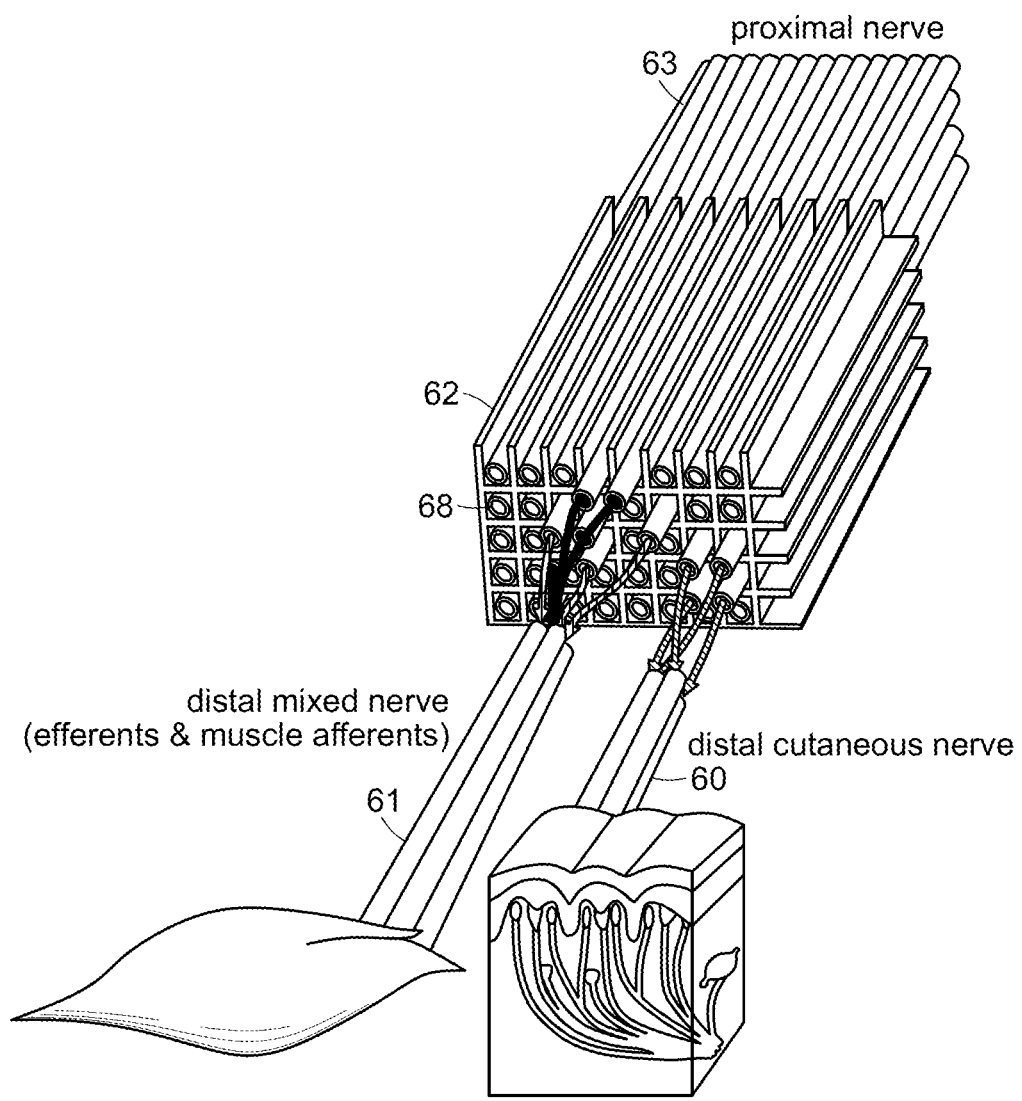
FIG. 9 is a schematic representation of the microchannel array of FIGS. 8A and 8B, wherein nerve fibers from a nerve proximal to an amputation site grow through the array and connect to target tissue nerves arranged on the other side of the array.
Figure 10:
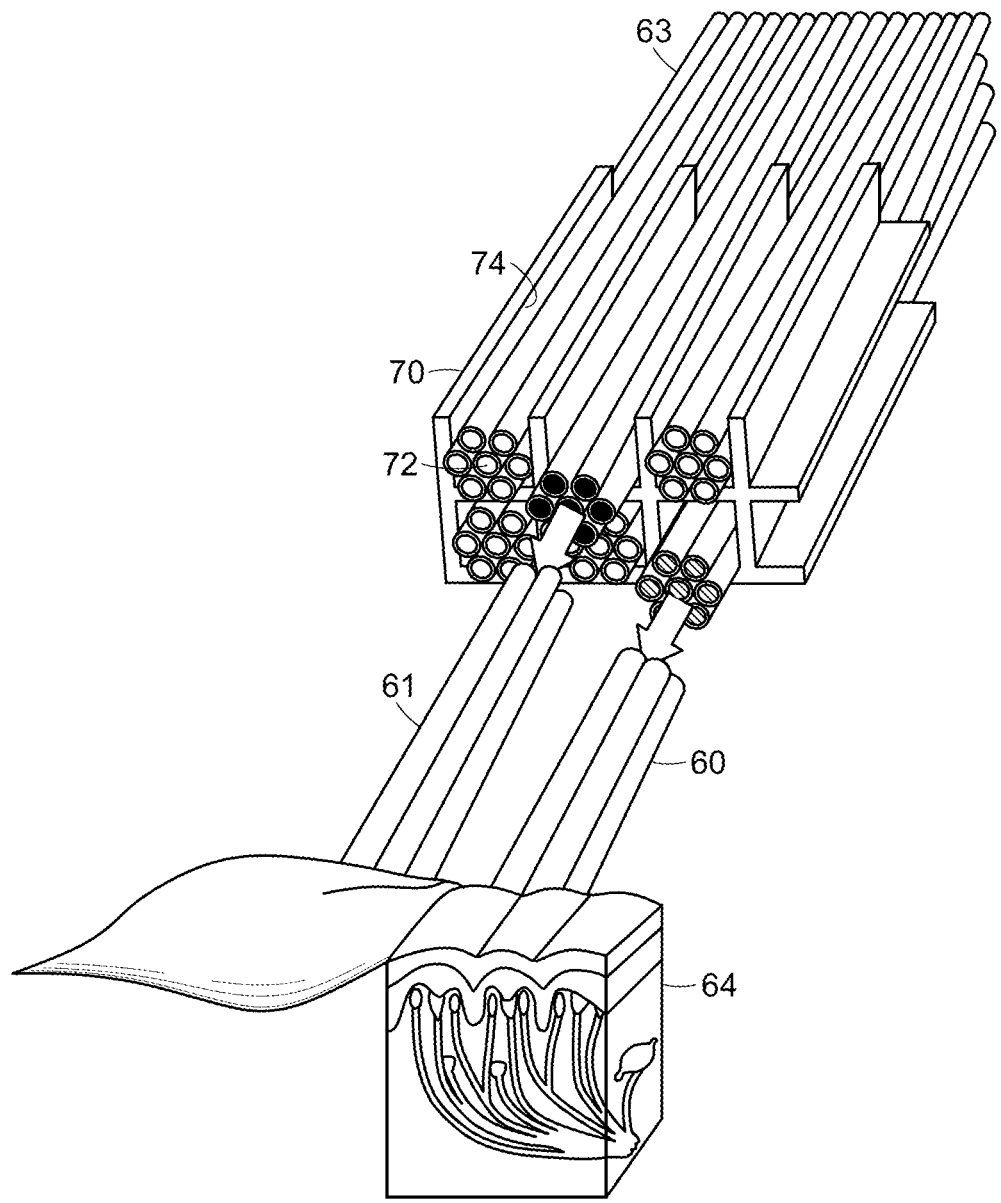
FIG. 10 is a schematic representation of another embodiment of the microchannel array of FIGS. 8A and 8B, wherein nerve fascicles from a proximal nerve in the residual limb are separated by function and placed into different channels of the array, whereby the fascicles regenerate through the array and reconnect to the native innervation of appropriate target tissues that have been relocated and arranged on the other side of the array.

FIG. 8A is a schematic representation of transecting nerves at target tissue 64 of a limb of an individual to thereby form distal ends 60, 61 and proximal ends 63 of the transected nerve, and of placing the distal ends 60, 61 and the proximal ends 63 of the transected nerves of target tissue 64 (e.g., muscle and skin) in a microchannel array 62, the microchannel array 62 including a bidirectional interface that (1) records afferent information of the nerve and (2) provides efferent stimulus to the nerve once the nerve has regenerated in the microchannel array, both through implanted electronics 65. FIG. 8B is a representation of one embodiment of placement of the microchannel array at the target tissue 64 of an individual and relative location of a prosthetic limb 66 controlled by the microchannel array 62. FIG. 9 is a schematic representation of the microchannel array 62 of FIGS. 8A and 8B, wherein nerve fibers 68 of proximal ends 63 at an amputation site grow through the microchannel array 62 and connect to distal ends 60, 61 arranged on the other side of the microchannel array 62. FIG. 10 is a schematic representation of another embodiment of the method of the invention that employs microchannel array 70 wherein nerve fascicles 72 from a proximal end 63 in the residual limb (not shown) are separated by function and placed into different channels 74 of the microchannel array 70, whereby the fascicles 72 regenerate through the microchannel array 70 and reconnect to the native innervation 60, 61 of appropriate target tissue 64, such as muscle and skin that have been relocated and arranged on the other side of the microchannel array 62.

A model for amputation surgery is described here, but as will be described in a subsequent section, such bi-directional neural interfaces can be implanted for the rehabilitation of spinal cord injuries, stroke, and other disabilities.

The neural interface devices (fabrication detailed in a later section) consist of an array of micro-channels with electrode contacts in each channel. These devices are implanted during an amputation surgery to guide nerve-to-nerve repairs between a nerve bundle proximal to the amputation site and a bundle of transected nerves from the amputated limb. When possible, the nerves from the amputated limb are relocated with their target tissues (either muscle or cutaneous) intact. This fourth embodiment serves the case where a nerve that subserves a target tissue that is to be relocated cannot be dissected intact along its entire length. In that case, the nerve is transected close to its target tissue, and the tissue with its short segment of attached nerve is relocated to the residual limb. The proximal continuation of the transected nerve in the residual limb is then grafted to the preserved segment of nerve attached to the target tissue. As depicted in FIG. 9, the proximal nerve in the residual limb is placed against one end of the micro-channel array, and individual nerve fibers are allowed to regenerate through the microchannels and eventually connect to target tissues on the distal side of the array. Target tissues and their innervation are arranged during surgery to mirror the arrangement of the respective nerve fascicles in the proximal nerve stump, and maximize the chance that nerve fibers regenerating through channels connect to their appropriate target tissues. In addition, as will be described subsequently, chemotropic substances are used to guide and sort nerve fiber regeneration through the micro-channel array.

Alternatively, in cases where fascicles are largely homogenous in function, it may be practical to employ channels with larger dimensions. In such cases, as illustrated in FIG. 10, the fascicles of the nerve in the residual limb can be separated and individually directed into channels of the array. The target tissue nerves are arranged on the distal side of the array in a way that maximizes the chances of the fascicles from the residual limb (proximal nerve stump) properly reconnecting to the correct target tissue nerves. When the nerve fibers from the proximal grafted nerve or grafted nerves regenerate through the micro-channels of the nerve interface, they form contacts with the channel electrodes, which in turn are wired to an implanted electronics module. As in the third embodiment, described above, this module wirelessly communicates with a controller mounted in the shell of the prosthesis. Every channel in the neural interfaces can seamlessly switch between recording and stimulation as needed; a neural interface can thus be configured as bi-directional, as desired for interfacing with a mixed proximal nerve, or the interface can be dedicated for stimulation only, as would be deployed for purely sensory nerves such as the saphenous or sural nerves of the leg. A single system can include multiple micro-channel array devices, each of which interfaces with the proximal continuation of a transected nerve in the residual limb.

Prosthetic motor commands are recorded from activity that the prosthetic user generates within the efferent motor nerve fascicles of interfaced nerves. Additional motor commands may be derived from recorded activity from surface or implanted electrodes, such as EMG electrodes, that may be placed over muscles native to the residual limb, as would be especially useful in the case of above-knee or above-elbow amputations. These electrodes would be wired to the same implanted electronics module that interfaces with all implanted micro-channel arrays. Sensory information is fed back to the user by electrically activating interfaced sensory afferent nerve fibers using coding techniques performed by onboard microprocessors that recreate natural sensations as much as possible. This may involve stimulating nerve fibers across multiple micro-channel array devices. The success of this strategy depends on the ability of an amputated peripheral nerve to regenerate into the interface device with a high degree of selectivity by function.

Several factors have been described that influence the ability of peripheral nerves to regenerate. Important among these is the presence of appropriate "target tissues" or end organs for the regenerating nerve fibers to reconnect with. Specifically, the axons of motor neurons need to reconnect to muscle tissue, while cutaneous sensory nerve fibers must reconnect to cutaneous sensory end organs, such as mechanoreceptors. The presence of target tissues provides chemotrophic substances to which the outgrowing neurites from a newly amputated nerve are attracted (G. Vrbova, N. Mehra, H. Shanmuganathan, N. Tyreman, M. Schachner, and T. Gordon, "Chemical communication between regenerating motor axons and Schwann cells in the growth pathway," European Journal of Neuroscience, vol. 30, no. 3, pp. 366-375, 2009). There is evidence that the chemical environment of motor nerves is slightly different from that of cutaneous sensory nerves, (G. Vrbova, N. Mehra, H. Shanmuganathan, N. Tyreman, M. Schachner, and T. Gordon, "Chemical communication between regenerating motor axons and Schwann cells in the growth pathway," European Journal of Neuroscience, vol. 30, no. 3, pp. 366-375, 2009; R. Martini, M. Schachner, and T. M. Brushart, "The L2/HNK-1 carbohydrate is preferentially expressed by previously motor axon-associated Schwann cells in reinnervated peripheral nerves," The Journal of Neuroscience, vol. 14, no. 11, pp. 7180-7191, 1994). In particular, this is in part due to subtle differences in the Schwann cells associated with motor and sensory axons. Because of this, it is useful to maintain a portion of the distal amputated nerve along with any transferred tissue that is intended to be used as a neural target tissue. Thus, the neural interface device, or micro-channel array, can be used as a mechanical connecting link or "bridge" between the proximal and distal segments of an amputated nerve as well as an electrical connection to the nerve. As a further exploitation of the chemotrophic effects that guide the outgrowth of regenerating peripheral nerves, it may be beneficial to "load" or "dope" the lumen of the various micro-channels of the interface with different chemotrophic species depending on which specific functional types of nerve fibers are intended to grow into the various micro-channels. It is also known that the mechanical and chemical features of various materials that can be loaded into the lumen of the micro-channels can influence which types of nerve fibers are most favored to grow into specific channels. Thus, a useful strategy to specify which types of nerve fibers will grow into which micro-channels of the interface is to vary the type of filler materials (that create extracellular matrices) and chemotrophic agents used in different micro-channels. Additionally, studies have demonstrated beneficial effects of providing immunosuppressant drugs in enhancing both the rate and completeness of peripheral nerve regeneration across gaps causes by nerve transection (I. Sosa, O. Reyes, and D. P. Kuffler, "Immunosuppressants: Neuroprotection and promoting neurological recovery following peripheral nerve and spinal cord lesions," *Experimental Neurology*, vol. 195, pp. 7-15, 2005).

Therefore, one embodiment of the method of the invention includes contacting the proximal and distal ends of a transected nerve with at least one of an immunosuppressant drug, a nerve growth factor, a chemotrophic drug, extracellular matrix material and neuronal support cells.

The provision of feedback information regarding joint motion and limb position is generally regarded as more challenging than is the case for tactile feedback. This stems mainly from the fact that (excluding direct visualization of the limb) limb motion and position sensibility is derived from several different receptor types in combination. Included among these is the state of stretch and relaxation of the skin that covers the opposing sides of the joint in question. Also, while it is known from single afferent microneurographic recordings that the slowly adapting cutaneous type II afferents located in the skin (at the back of the hand) that covers the finger joints fire in response to finger flexion (B. B. Edin and J. H. Abbs, "Finger movement responses of cutaneous mechanoreceptors in the dorsal skin of the human hand," Journal of Neurophysiology, vol. 65, pp. 657-670, 1991), microstimulation of these same afferent nerve fibers individually, fails to evoke any sensory experience of skin stretch or finger motion in intact human subjects (J. Ochoa and E. Torebjork, "Sensations evoked by intraneural microstimulation of single mechanoreceptor units innervating the human hand," Journal of Physiology, vol. 342, pp. 633-654, 1983). It is hypothesized that it may be necessary to simultaneously activate a number of such afferents in order to reach a threshold for sensory awareness. Thus, success in employing cutaneous stretch sensitive afferents for joint position feedback using the micro-channel interface may rely on being able to activate several related stretch sensitive (SAII) afferents at the same time.

In a closed-loop paradigm between a human and a wearable device, sensory information recorded using synthetic sensors on the external device and/or human is mapped to appropriate afferent signals using microprocessor(s) located on the wearable device. After this computational step, stimulation commands are sent wirelessly to the implanted electronics that causes electrical stimulations through the microchannel array or arrays. The character and magnitude of these nerve stimulations will vary depending on the type of sensory feedback and the strength of that feedback. Such afferent signaling enables the human wearer to better modulate descending motor efferent signals that are recorded using the electrodes within the array channels for motor nerve fascicles. Alternatively, implanted muscle electrodes for sensing signal activity, such as EMG signal activity, could be used as was described in embodiment three. Such muscle signals are communicated wirelessly by the implanted electronics to the external prosthetic microprocessor(s) that then control motor(s) to drive the prosthesis.

Fifth Embodiment

Figure 11A:
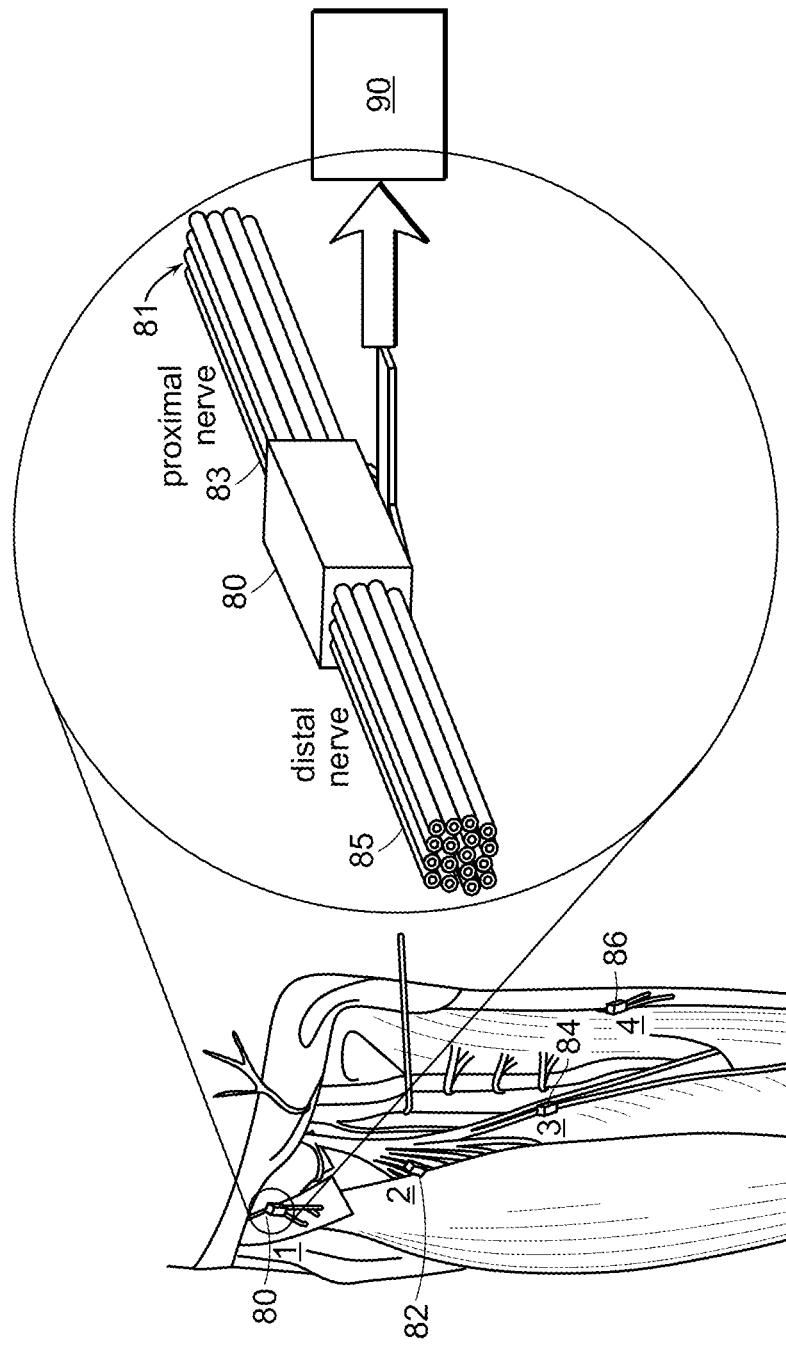
FIG. 11A is a schematic representation of still another microchannel array employed by at least one embodiment of the method of the invention, wherein nerves in a paralyzed limb affected by a motor impairment disability (e.g., spinal cord lesion) are transected, and micro-channel array devices are placed between the proximal and distal nerve stumps whereby, after nerve regeneration, the limb may be controlled via artificial muscle stimulations using sensory recordings from channels within the implanted array devices.
Figure 11B:
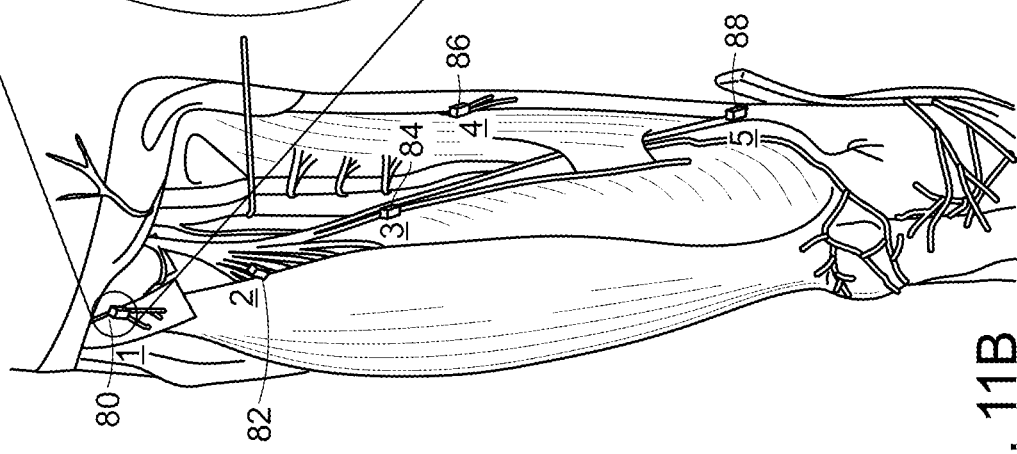
FIG. 11B is a representation of placement of the microchannel array of FIG. 11A.

In a fifth embodiment of the invention, represented schematically in FIGS. 11A and 11B, the method of the third or fourth embodiments described above further includes the step of correlating recorded afferent signals from the microchannel array 80 in an algorithm to generate motor-efferent signals at the microchannel array 80 and thereby reverse motor impairment of the human limb. In a particular embodiment, the method includes linking signals associated with the microchannel array 80 with signals associated with a second microchannel array 82 at a second transected and regenerated nerve, and coordinating recorded sensory afferent signals and motor stimulation efferent signals of one microchannel array with signals of the second microchannel array, and so on for additional microchannel arrays 84, 86, 88.

Neural interfacing has become an important component of systems for the rehabilitation of several disability conditions. Among these is the rehabilitation of spinal injury using "Functional Electrical Stimulation Systems," or "FES." Using various styles of cuff electrodes, for example, developers have produced clinically useful systems that restore motor function from otherwise paralyzed muscles by electrically activating the interfaced nerves. Such systems can restore grasping ability to quadriplegic individuals (P. H. Peckham, B. Smith, J. R. Buckett, G. B. Thrope, J. E. Letechipia, "Functional muscle stimulation system," U.S. Pat. No. 5,769,875, Jun. 23, 1998), standing and walking to paraplegics (G. P. Forrest, T. C. Smith, R. J. Triolo, J. Gagnon, D. DiRisio, M. E. Miller, and L. Rhodi, "Use of the Case Western Reserve/Veterans Administration neuroprosthesis for exercise, standing and transfers by a paraplegic subject," Disability and Rehabilitation Assistive Technology, vol. 7, no. 4, pp. 340-344, 2012), and correct foot-drop in individuals following stroke injury (M. Haugland and T. Sinkjaer, "Cutaneous whole nerve recordings used for correction of foot drop in hemiplegic man," IEEE Transactions on Biomedical Engineering, vol. 3, no. 4, pp. 307-317, 1995). Aside from limb mobility, FES techniques have also been successfully applied to provide control over other motor functions such as bowel and bladder function (G. S. Brindley, C. E. Polkey, D. N. Rushton, and L. Cardozo, "Sacral anterior root stimulators for bladder control in paraplegia: the first 50 cases," Journal of Neurology, Neurosurgery, & Psychiatry, vol. 49, no. 10, pp. 1104-14, 1986), and diaphragm pacing for ventilation (M. Sahin, D. M. Durand, and M. A. Haxhiu, "Chronic recordings of hypoglossal nerve activity in a dog model of upper airway obstruction," Journal of Applied Physiology, vol. 87, no. 6, pp. 2197-2206, 1999). Furthermore, the ability to activate sensory nerves using an electrical neural interface can be applied to restoring vision in some blind populations (C. Veraart, M. C. Wanet-Defalque, B. Gerard, A. Vanlierde, and J. Delbeke, "Pattern recognition with the optic nerve visual prosthesis," Artificial Organs, vol. 27, no. 11, pp. 996-1004, 2003, and providing hearing ability to many otherwise deaf individuals, G. E. Loeb, "Cochlear prosthetics," *Annual Review of Neuroscience*, vol. 13, pp. 357-371, 1990).

With the exception of auditory neuroprostheses, rehabilitation systems that rely on neural interfaces have mostly provided for the activation of motor nerves. However, it is also possible to record from sensory nerves to obtain feedback information, as described in the third and fourth embodiments, that can be used in "closed-loop" control algorithms for restoring biological functions in disability. Some examples that have been explored have involved sensing bladder "fullness" by recording from the pudendal nerve (S. Jezernik, W. M. Grill, and T. Sinkjaer, "Detection and inhibition of hyperreflexia-like bladder contractions in the cat by sacral nerve root recording and electrical stimulation," Neurourology and Urodynamics, vol. 20, no. 2, pp. 215-230, 2001), sensing foot-floor contact for controlling an FES-based foot-drop neuroprosthesi (M. Haugland and T. Sinkjaer, "Cutaneous whole nerve recordings used for correction of foot drop in hemiplegic man," IEEE Transactions on Biomedical Engineering, vol. 3, no. 4, pp. 307-317, 1995), and recording from the digital nerve of the thumb to sense grip force and slippage in a grasp restoration neuroprosthesis (M. Haugland, A. Lickel, R. Riso, M. M. Adamczyk, M. Keith, I. L. Jensen, J. Haase, and T. Sinkjaer, "Restoration of lateral hand grasp using natural sensors," Artificial Organs, vol. 21, no. 3, pp. 250-253, 1997). All of these motor and sensing applications would be vastly more effective if the specificity of the neural interface, as well as its ability to more completely sample the targeted nerve, was enhanced. Optimal specificity would allow the motor nerves innervating each individual muscle to be addressed in isolation. With regard to sensory applications, the afferent nerve fibers that subserve each different sensory modality would need to be differentially addressable for stimulation and for recording. Additionally, sensory fibers that project to different body regions should be accessible without undesired overlap.

In this embodiment, the method of the invention includes reversing the impairment of an amputated limb, including inserting a distal end of at least one transected nerve of an amputated limb into a proximal end of a microchannel array, placing at least one member of the group consisting of skin and muscle end organ at the distal end of the microchannel array, thereby causing the nerve to regenerate through the microchannel array and to innervate the at least one end organ. Efferent motor information of the regenerated nerve is recorded using sensing electrodes within a plurality of efferent microchannels of the microchannel array. The regenerated nerve is stimulated with afferent sensory information using stimulating electrodes within a plurality of afferent microchannels of the microchannel array. The sensing electrodes are electrically connected to a motor controller of a device. The stimulating electrodes are electrically connected to a sensory controller of the device, wherein the motor controller is linked to at least one sensor of the device that detects application of at least one member selected from the group consisting of position, velocity, acceleration, and force of the device, and whereby the motor controller transmits detection of the position, velocity, acceleration, and force by applying electrical stimulation via the stimulating electrodes, thereby providing the individual with a sensation simulating sensory feedback from the device, and reversing impairment of the amputated limb.

The micro-channel nerve interface proposed herein is designed to achieve significantly improved specificity for stimulation and recording of peripheral nerve fibers, as well as exceptional long-term stability and efficacy. In the fourth embodiment, the micro-channel array was described for use in a novel limb amputation model. The fifth embodiment, depicted schematically in FIGS. 11A and 11B, describes the more generalized application of the micro-channel array for motor impairment disabilities such as spinal cord lesion and stroke. For the fifth embodiment, a nerve 81 is transected in the affected limb that has experienced paralysis from a spinal cord lesion or stroke condition. The micro-channel array is then placed between proximal 83 and distal 85 nerve stumps. Through the application of factors that enhance nerve regrowth and reconnection, such as immune suppressant drugs and nerve growth factors within the micro-channel array, the proximal nerve would regenerate through the micro-channel array, reconnecting to the distal tissue organs, in a nerve-to-nerve repair. Subsequent to the nerve's full regeneration, in a bi-directional control paradigm, sensory afferent information from the distal biological limb, or biological member, could be recorded from channels within the implanted microchannel arrays 80, 82, 84, 86, 88 with high specificity, and then employed in an artificial feedback algorithm to determine appropriate levels of motor stimulus to be applied to distal limb muscles through motor channels within the same micro-channel array, or an alternate microchannel array attached to an alternate nerve. In the general case of a limb that has suffered full paralysis, each major nerve of the limb could be transected and a micro-channel array inserted for nerve regeneration. Upon regeneration through all the micro-channel arrays, mathematical mapping could be applied, linking recorded sensory afferents from the distal limb and stimulation efferents to evoke limb muscle activations for a whole host of stationary and movement patterns, including standing, walking and grasping. Such a mathematical mapping would essentially replicate the dormant spinal reflexes in an artificial spinal computational framework. The artificial processor(s) to perform such computations could be positioned external to the body, where recorded efferents and commanded motor afferents are received and transmitted between the computational module worn externally on the patient (not shown) and implanted neural electronics 90.

In the next section, the micro-channel nerve interface proposed herein for the fourth and fifth embodiments are described.

Design and Fabrication of Micro-Channel Nerve Interface Physical Structure—

A central element of the method of the fourth and fifth embodiments is a structure comprising an array of micro-channels that contain electrode contacts for recording and stimulating nerve fibers. Depending on the application needs, some of the micro-channels may not contain electrodes. The addition of open channels (with or without electrodes) provides more places for regenerating nerve fibers to grow into. This can be beneficial because it has been shown that nerve regeneration is more robust when the "transparency factor" of the interface is greater (i.e. there is more open space vs. blockage facing the advancing edge of the regenerating nerve).

Figure 12:
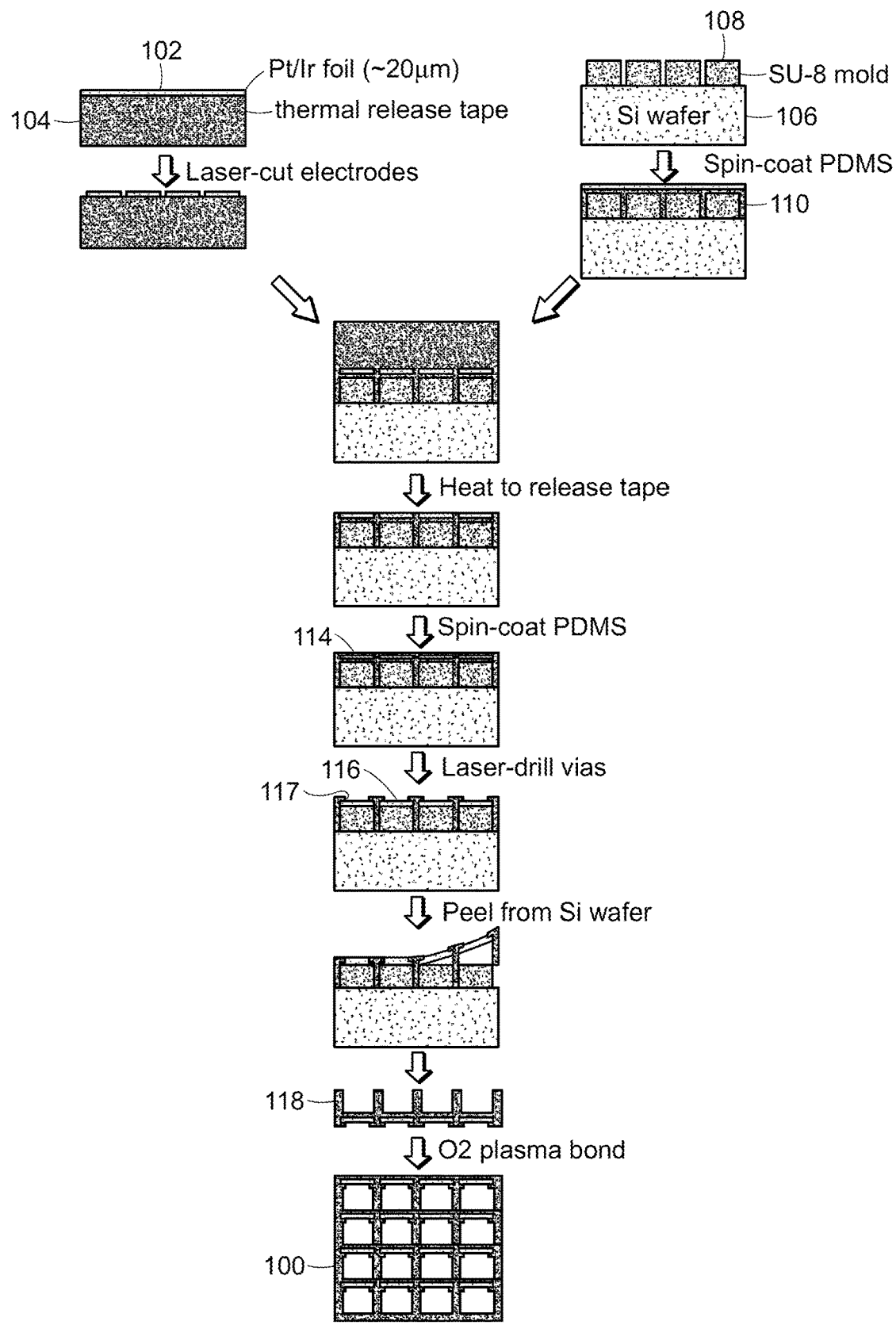
FIG. 12 is a schematic representation of one embodiment of a method for fabricating a three-dimensional array suitable for use by at least one embodiment of the method of the invention.

FIG. 12 illustrates one design configuration for fabricating a three-dimensional microchannel array 100 complete with addressable electrode structures. The array is made from silicone (PDMS), a biologically inert material widely used in implants, and is fabricated in a layer-by-layer process. Other materials—either natural or synthetic—with suitable properties may also be employed. First, a ~20 μm Pt/Ir foil 102 is laminated onto a thermal release tape (e.g. REVALPHA) or UV release tape 104. This foil is patterned into electrodes using a UV laser micromachining system, which has the capability to form feature sizes <100 μm. Excess foil is peeled away with tweezers. On a silicon wafer carrier 106, a micro-channel SU-8 photoresist mold 108 is created using standard photolithography techniques, and PDMS 112 is spun onto this wafer to create PDMS microchannels 110. The PDMS 112 is partially cured at 65 C for ~15 minutes, at which point the electrode layer is aligned and pressed into the PDMS 112. This stack is left to fully cure under pressure at a temperature high enough to allow the thermal release tape to lose its adhesion and be peeled away. Another thin (~20 μm) PDMS 114 layer is next spun onto the substrate to insulate the electrodes. The laser micromachining system is used to drill holes 117 in the PDMS insulating layer 114 to the underlying metal electrodes to provide electrical contact sites 116 within each channel. This stack, which forms one layer of the microchannel array 100, is then peeled away from the SU-8 mold 108. Multiple micro-channel layers 118 are aligned and stacked upon one another to complete the array 100. This is achieved by exposing bonding surfaces to a low-pressure (~80 mTorr) oxygen RF plasma, which increases the density of silanol (Si—OH) groups on the PDMS surfaces. The treated surfaces are mated, allowing silanol groups to form permanent covalent Si—O—Si bonds between the surfaces. Finally, medical-grade wires (not shown) can be laser-welded to the metal interconnects 116 from the array for connection to an implanted control module or percutaneous connector (not shown). With this process, channels with widths of ~20 µm up to hundreds of µm can be fabricated with channel separations as small as ~20 µm.

The number of micro-channels in each array and the size and geometry of each micro-channel are arbitrary depending on the application, and it is possible to have different sized channels intermixed with each other. Larger channels would allow greater numbers of nerve fibers to grow into them, enabling the sampling of a greater number of nerve fibers to provide a higher amplitude signal (if the fibers were activated concomitantly). A narrow channel could increase the specificity of the nerve recordings by reducing the number of sampled fibers.

FIG. 13A is an exploded view of one embodiment of a three-dimensional microchannel array 120 suitable for use by at least one method of the invention. Shown are channels 122 and interconnects 124. FIG. 13B is a perspective view of the assembled three-dimensional microchannel array 120 of FIG. 13A.

Other Design Considerations of the Novel Peripheral Nerve Interface:

Modularity—An advantage of the micro-channel design is that the physical dimensions of the implant device can be customized depending on the size and fascicular structure of the targeted nerve or nerves. This can be done simply by changing the mask used during photolithography or by combining two or more smaller arrays.

Use of Target Tissues—The novel design of the nerve interface makes use of "target tissues" which assists the regenerating proximal sensory and motor nerve fibers to re-connect with their appropriate end organs harvested from the distal limb. This assures that the regenerated nerve will be stable over the long term so that a neural-based control system does not have to be "tuned" or modified often.

Moreover, the incidence of neuroma formation is substantially reduced when the outgrowing nerve fibers from a transected peripheral nerve are constrained and are able to reconnect with their preferred target tissues, (J. T. Aitken, "The effect of peripheral connexions on the maturation of regenerating nerve fibres", Journal of Anatomy, vol. 83, no. 1, pp. 32-43, 1949); A. L. Dellon and S. E. Mackinnon, "Treatment of the painful neuroma by neuroma resection and muscle implantation," Plastic and Reconstructive Surgery, vol. 77, no. 3, pp. 427-38, 1986; and T. Okuda, O. Ishida, Y. Fujimoto, N. Tanaka, A. Inoue, Y. Nakata, and M. Ochi, "The autotomy relief effect of a silicone tube covering the proximal nerve stump," Journal of Orthopaedic Research, vol. 24, number 7, pp. 1427-37, 2006). An important benefit of this is that the possibility for the development of phantom limb pain is then substantially lowered as well (H. Cravioto and A. Battista, "Clinical and ultrastructural study of painful neuroma," Neurosurgery, vol. 8, no. 2, pp. 181-90, 1981).

Use of Chemotropic Agents—Chemo-attractants may be added to the interface device to direct the regrowth of different types of nerve fibers differentially. It is possible to add extracellular matrix materials as well as neurotrophic substances to specific micro-channels in an effort to achieve separation among the various types of regenerating motor and sensory nerve fibers. These efforts may also include the use of neuronal support cells, such as Schwann cells, that are specific for different types of nerve fibers (G. Vrbova, N. Mehra, H. Shanmuganathan, N. Tyreman, M. Schachner, and T. Gordon, "Chemical communication between regenerating motor axons and Schwann cells in the growth pathway," European Journal of Neuroscience, vol. 30, no. 3, pp. 366-375, 2009; and R. Martini, M. Schachner, and T. M. Brushart, "The L2/HNK-1 carbohydrate is preferentially expressed by previously motor axon-associated Schwann cells in reinnervated peripheral nerves," The Journal of Neuroscience, vol. 14, no. 11, pp. 7180-7191, 1994).

Sixth Embodiment

In a sixth embodiment, the invention is directed to a method for simulating a proprioceptive sensory organ for a limb or organ, and includes mechanically linking at least one pair of agonist and antagonist muscles. In one embodiment, at least one of the muscles of at least a portion of the pairs of agonist and antagonist muscles includes at least one member selected from the group consisting of a Golgi tendon organ, muscle spindle stretch fibers, and an efferent/afferent nerve. In one specific embodiment, the Golgi tendon organ, the muscle spindle stretch fiber or afferent/efferent nerve is preserved intact. At least one pair of agonist and antagonist muscles are supported, whereby contraction of the a muscle of each pair causes extension of the paired muscle. In one embodiment, the Golgi tendon organ of the agonist muscle and the spindle stretch fibers of the antagonist muscle will generate afferent signals. An electrode, such as an electromyographic electrode, is implanted in each of the agonist and antagonist muscles of each pair. In one embodiment, the electrode senses and stimulates muscle contraction. The electrodes are electrically connected to a motor controller of a device. In one embodiment, the device includes at least one member selected from the group consisting of a prosthesis, orthosis or exoskeleton. In one embodiment, a position about a degree of freedom of the device can be sensed by an individual wearing the device, the agonist and antagonist muscles, thereby simulating a proprioceptive sensory organ for a human limb or organ.

This embodiment describes novel Regenerative Peripheral Nerve Interface (RPNI) models for providing 1) efferent motor agonist/antagonist signals for the control of external prosthetic motors, and 2) proprioception and cutaneous afferent feedback into peripheral nerves from external prosthetic sensory signals. The proposed models are unique in their potential capacity to utilize native tissue mechanoreceptors to translate prosthetic sensory information related to muscle stretch and tension, as well as skin pressure and shear, into neural signals similar to those experienced in the normal biological milieu. In contrast to alternative approaches to afferent feedback that bypass native biological tissues, the proposed models incorporate the specialized biomechanical structures inherently present in muscle and skin to transduce information regarding muscle fascicle state and force, as well as skin mechanoreceptor strain. In utilizing biological structures in the design of these systems, when integrated with current state-of-the-art bionic limb prostheses, amputees are expected to experience proprioceptive and cutaneous sensory feedback that approximates or equals that of their previously uninjured state while simultaneously providing a safe and viable peripheral neural interface.

These designs extend the functionality of traditional RPNIs, as previously described by the seminal work of Cederna et al. (M. G. Urbanchek, J. D. Moon, K. B. Sugg, N. B. Langhals, P. S. Cederna, Z. Baghmanli, "Regenerative peripheral nerve interface function at 1 and 3 months after implantation," *Plastic & Reconstructive Surgery*, vol. 130, no. 1S, pp. 84, 2012). A traditional RPNI is a surgical construct in which a segment of nonvascularized muscle is approximated with the distal terminus of a peripheral nerve and is subsequently reinnervated to provide a stable biological substrate for neural interaction. To date, RPNIs have been described primarily as a means to achieve efferent motor signals from a single muscle construct constrained to only generate isometric force; when innervated by a peripheral motor nerve, the isometric muscle unit serves as an amplifier of neural activation that may be recorded using standard EMG electrodes and used for the control of synthetic actuators in an external prosthesis (C. M. Frost, D. C. Ursu, A. Nedic, C. A. Hassett, J. D. Moon, S. L. Woo, R. B. Gillespie, P. S. Cederna, N. B. Langhals, M. G. Urbanchek, "Neuroprosthetic hand real-time proportional control by rodent regenerative peripheral nerve interfaces," Plastic & Reconstructive Surgery, vol. 133, no. 4S, pp. 1012-3, 2014). However, since the muscle is held isometrically, realistic muscle fascicle strains cannot be achieved. Further, an antagonist muscle is not stretched when the innervated agonist contracts, eliminating realistic spindle fiber feedback from the antagonist when an external prosthetic joint flexes. Finally, current motor RPNI technology does not allow the force on the innervated muscle construct to be modulated by an antagonist muscle so as to allow force feedback from an external prosthesis.

More recently, sensory RPNIs have been demonstrated (J. V. Larson, M. G. Urbanchek, J. D. Moon, D. A. Hunter, P. Newton, P. J. Johnson, M. D. Wood, T. A. Kung, P. S. Cederna, and N. B. Langhals, "Prototype sensory regenerative peripheral nerve interface for artificial limb somatosensory feedback," Plastic & Reconstructive Surgery, vol. 133, no. 3S, pp. 26-27, 2014). Here, afferent signaling in principle can be achieved by having a sensory nerve innervate an isometric muscle component, and then artificially stimulating that innervated muscle to modulate the afferent signal. Although a critically important step forward for the field, such an RPNI design does not incorporate native skin mechanoreceptors for realistic skin strain feedback. Further, the design has not been tested in human subjects to provide a means of assessing how such non-specific afferent signaling from contracting isometric muscle fibers would be perceived.

Proprioceptive Muscle RPNI (Pro-m-RPNI)

The fundamental motor unit to control a biological joint is an agonist-antagonist muscle-tendon pair. Such a muscle-tendon relationship allows organisms to simultaneously control joint state (position and speed) and impedance (stiffness and damping) for upper and lower extremity motor tasks. At least one pair of antagonistic muscles are needed for each degree of freedom of a limb in order to control both joint state, torque and impedance. Although only one Pro-m-RPNI is described per prosthetic degree of freedom, it should be understood by those of ordinary skill in the art that a plurality of Pro-m-RPNI devices could be employed in the control of each degree of freedom of a prosthetic, orthotic or exoskeletal limb.

A major input to joint state afferent sensory information derives from the muscle spindle receptors which are known to discharge when a muscle is passively elongated, but which stop firing abruptly whenever that muscle is slackened passively (R. R. Riso, F. K. Mosallaie, W. Jensen, and T. Sinkjær, "Nerve cuff recordings of muscle afferent activity from tibial and peroneal nerves in rabbit during passive ankle motion," IEEE Transactions on Rehabilitation Engineering, vol. 8, no. 2, pp. 244-258, 2000). When a muscle undergoes an active contraction, however, the discharges from spindle receptors within that muscle could halt or be modified, depending on any activation of spindle intrafusal muscle fibers via Gamma motor neurons (M. Hulliger, "The mammalian muscle spindle and its central control," Reviews of Physiology, Biochemistry and Pharmacology, vol. 101, pp. 1-110, 1984).

In yet another embodiment of the invention, the method includes simulating proprioceptive sensory feedback from a device, including the steps of the mechanically linking at least one pair of agonist and antagonist muscles, wherein a nerve innervates each muscle. The at least one pair of agonist and antagonist muscles are supported with a support, whereby contraction of the agonist muscle of each pair will cause extension of the paired antagonist muscle. At least one electrode is implanted in at least one muscle of each pair, and the at least one electrode is electrically connected to a motor controller of the device, thereby stimulating proprioceptive sensory feedback from the device.

Figure 14:
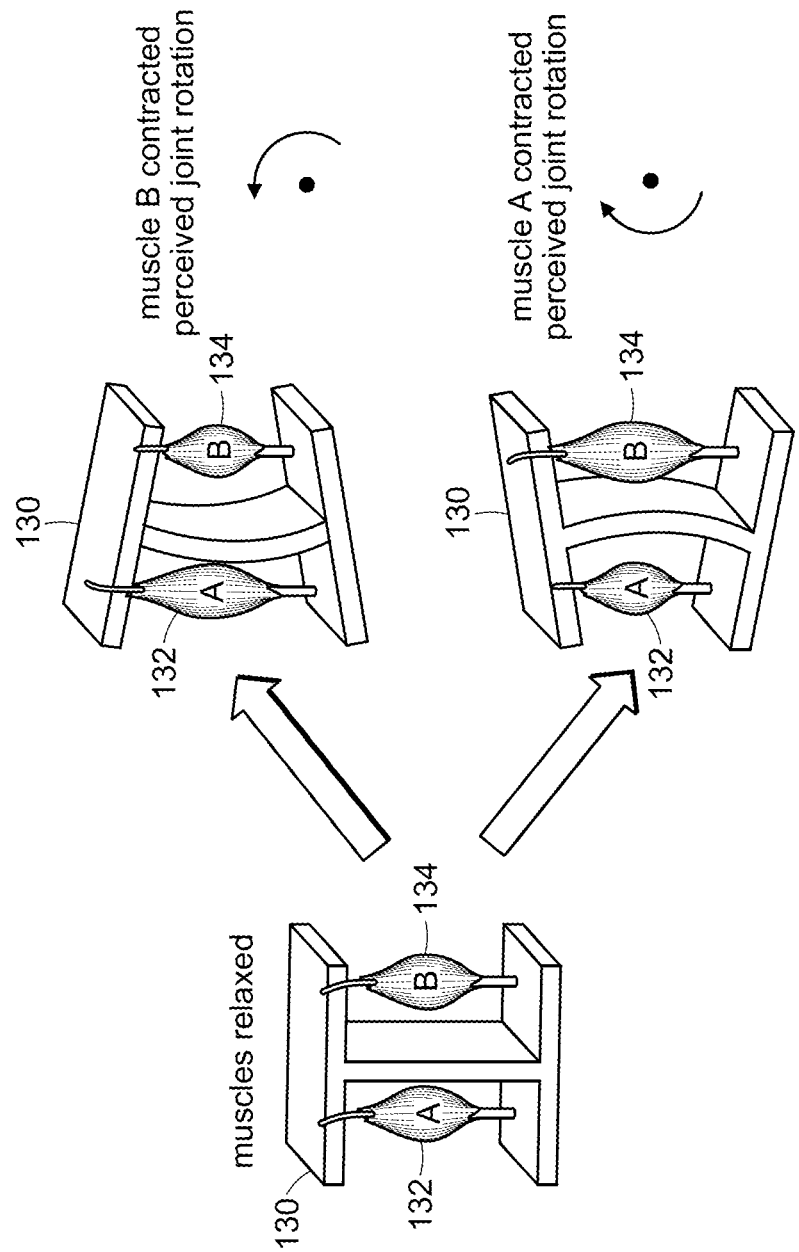
FIG. 14 is schematic representation of supporting at least one pair of agonist and antagonist muscles by one embodiment of the method of the invention, whereby contraction of the agonist muscle of each pair will cause extension of the paired antagonist muscle, and whereby the agonist-antagonist muscle pair provide proprioceptive information about movement and impedance via activity generated from the muscle spindle and tendon afferents of the agonist-antagonist muscle pair.

FIG. 14 depicts the coupling of an agonist-antagonist muscle pair using a flexible "I-beam joint" structure 130. As illustrated in FIG. 14, when a muscle 132 on one side of a I-beam joint structure contracts (e.g., muscle A) and moves the joint 130, this motion elongates the muscle 134 that is attached to the opposite side of the joint 130 (e.g., muscle B) and causes the muscle 134 spindle receptors to discharge. Similarly, if contraction of muscle 134 causes the joint 130 to rotate towards the opposite direction, then muscle 132 will be elongated causing the muscle 132 spindle receptors to discharge. Presumably, the arithmetic difference between the activity levels of muscle 132 and muscle 134 spindle afferents would be representative of the "joint" 130 position. This thesis is supported by studies in which the flexor and extensor tendons of the biceps and triceps muscles in the fixated arm of normal human subjects were vibrated individually or the flexor and extensor tendons were vibrated simultaneously (J. P. Roll and J. P. Vedel, "Kinesthetic role of muscle afferents in man, studied by tendon vibration and microneurography," *Experimental Brain Research*, vol. 47, no. 2, pp. 177-190, 1982), (the vibratory stimulus causes the spindle receptors in the vibrated muscle to discharge). When the biceps tendon was vibrated alone, subjects reported a sensation that the elbow was extending, whereas if the triceps tendon was vibrated alone the subjects perceived that their elbow was moving in the flexion direction. Faster vibration resulted in a higher perceived velocity of the limb motion. Finally, if the biceps and triceps tendons were vibrated at the same time and using the same frequency, then the elbow position was perceived to remain stationary. However, if the frequency of vibration was different for the biceps and triceps during the simultaneous vibration studies, then the perception of limb movement was toward flexion when the triceps was driven at the faster frequency and the motion was perceived toward extension if the biceps received the faster vibratory stimulation.

This "push-pull" system that exists on each side of a joint in normal physiology can be mimicked when transferring muscles by placing them in opposition to each other using some kind of mechanical system that couples their movements to each other. One mechanical design that could accomplish this coupling is the compliant I-beam device shown in FIG. 14. Such a mechanical structure could be fabricated from various materials having arbitrary stiffness profiles at the points of muscle attachments and for the deformable beam that connects to the pair of tethered muscles.

To achieve an agonist-antagonist interaction, other muscle-tendon configurations are possible. Alternative configurations to the aforementioned I-beam structure are the Pro-m-RPNIs shown in FIG. 15-17. These configurations incorporate motor RPNIs from discrete agonist-antagonist muscle pairs (e.g. ECRB and FCR) attached in series. In one case, shown in FIG. 15, the muscles 143 and 145 of muscle pair 140, with their native Golgi tendon organs 142 and intrafusal muscle spindle stretch fibers 144, are sutured or bonded together tendon-to-tendon at one end 146 to form a series combination. The two free ends 148, 150 of the linearly-coupled, muscle-tendon arrangement are then secured to a biological or synthetic structure. Ideally, the linear RPNI is simply secured to bone 152 to avoid the difficulty of making a biological-to-synthetic interface. When a synthetic material must be used, as illustrated in FIG. 16, the structure may be made of a stiff material 154, such as titanium, or a more compliant one, such as silicone, as desired. Depending on the material of the structure, a small piece of the bone at the native tendon-bone attachment site may be preserved to enable the attachment of the muscle-tendon piece to the structure. FIG. 17 is a representation of a Pro-m-RPNI schematic about a synthetic spool shown comprising: 1) a synthetic spool; 2) an agonist muscle; 3) an agonist motor/afferent nerve; 4) an agonist electrode for electromyographic sensing and functional electrical stimulation; 5) agonist muscle spindle fibers; 6) an agonist Golgi tendon organ; 7) an antagonist muscle; 8) an antagonist motor/afferent nerve; and 9) an antagonist electrode for electromyographic sensing and functional electrical stimulation. As shown in FIG. 17, Pro-m-RPNI muscle pair 155 is secured into a loop around a low-friction synthetic spool 158. Contraction of the agonist muscles 143,156 via the standard motor nerves 141,157 efferent of one muscle will provide electrode signaling, such as EMG signaling, by the antagonist muscles 145,159 to an external prosthetic actuator through electrodes 147,161 as in a standard motor RPNI; however, it will simultaneously activate the native contractile mechanoreceptors in the Golgi tendon organs 142,163 of the agonist muscles 143,156, as well as the native intrafusal muscle spindle stretch fibers of the mechanically-coupled antagonist muscles 145,159, both of which will provide afferent proprioceptive signaling through the sensory components of their respective innervation nerves. Subsequent volitional activation of the antagonist muscles 145,159 will stimulate a complimentary stretch on the agonist muscles 143,156; as such, this proprioceptive RPNI will demonstrate a more realistic agonist-antagonist mechanical coupling providing non-isometric fascicle strains and agonist-antagonist fascicle state spindle feedbacks.

While this strategy may seem simple conceptually, because muscle spindle receptors exist in several different varieties with each having slightly different response properties (A. B. Vallbo, "Basic patterns of muscle spindle discharges in man," in *Muscle Receptors and Movement*, A. Taylor and A. Prochazka, Eds. London: Macmillan, 1981, pp. 263-275), it would be best if the innervation to a selected pair of agonist and antagonist muscles is able to be left intact to those muscles so that the brain can interpret the spindle discharge information with minimal retraining. In cases where the translocated muscle requires that its innervation be replaced by nerve repair (where some misconnection of some afferent fibers to end organs may occur), practical experience with implanted amputee subjects will determine if mechanisms of cortical plasticity are able to interpret the sensory afferent activity from the reconnected spindle and tendon receptors sufficiently to provide satisfactory information regarding joint motion, position and force.

Furthermore, the Pro-m-RPNI framework will also allow force feedback from Golgi tendon organs within the agonist and/or antagonist. When the agonist contracts, for example, the level of antagonist activation or co-contraction, will determine the force borne by the agonist, and such a force will be communicated as an afferent signal through the sensory components of its respective innervation nerve.

For the Pro-m-RPNI, electrodes are placed over each muscle of the agonist-antagonist pair. Such electrodes can be used for motor intent acquisition by recording muscle electromyography (EMG) for use as a prosthetic control signal. The level of common mode muscle activation, or co-contraction, measured by the EMG electrodes on the agonist-antagonist muscle pair, can be used to determine the user's intent for prosthetic joint impedance (stiffness and damping). In distinction, the differential in measured EMG signals can be employed to determine joint state (position/speed).

In addition, such electrodes can apply functional electrical stimulation (FES) for prosthetic force feedback from an external prosthesis; by applying FES on the antagonist as the agonist contracts, the force on the agonist can be controlled by the external prosthetic processors based upon synthetic force sensory information from the corresponding prosthetic joint. For example, when an upper extremity prosthetic user picks up a bar bell weight and flexes her prosthetic wrist, the Pro-m-RPNI corresponding to wrist flexors/extensors can be electrically stimulated so the user can experience the bar bell weight; as the Pro-m-RPNI agonist muscle contracts, with a motor nerve supply that once innervated the wrist flexors prior to limb amputation, an FES control can be applied to the Pro-m-RPNI antagonist muscle, increasing the force borne by the agonist. The magnitude of the FES stimulation signal would be proportional to the estimated force that would have been applied by the wrist flexors against the bar bell load prior to limb amputation.

Figure 15:
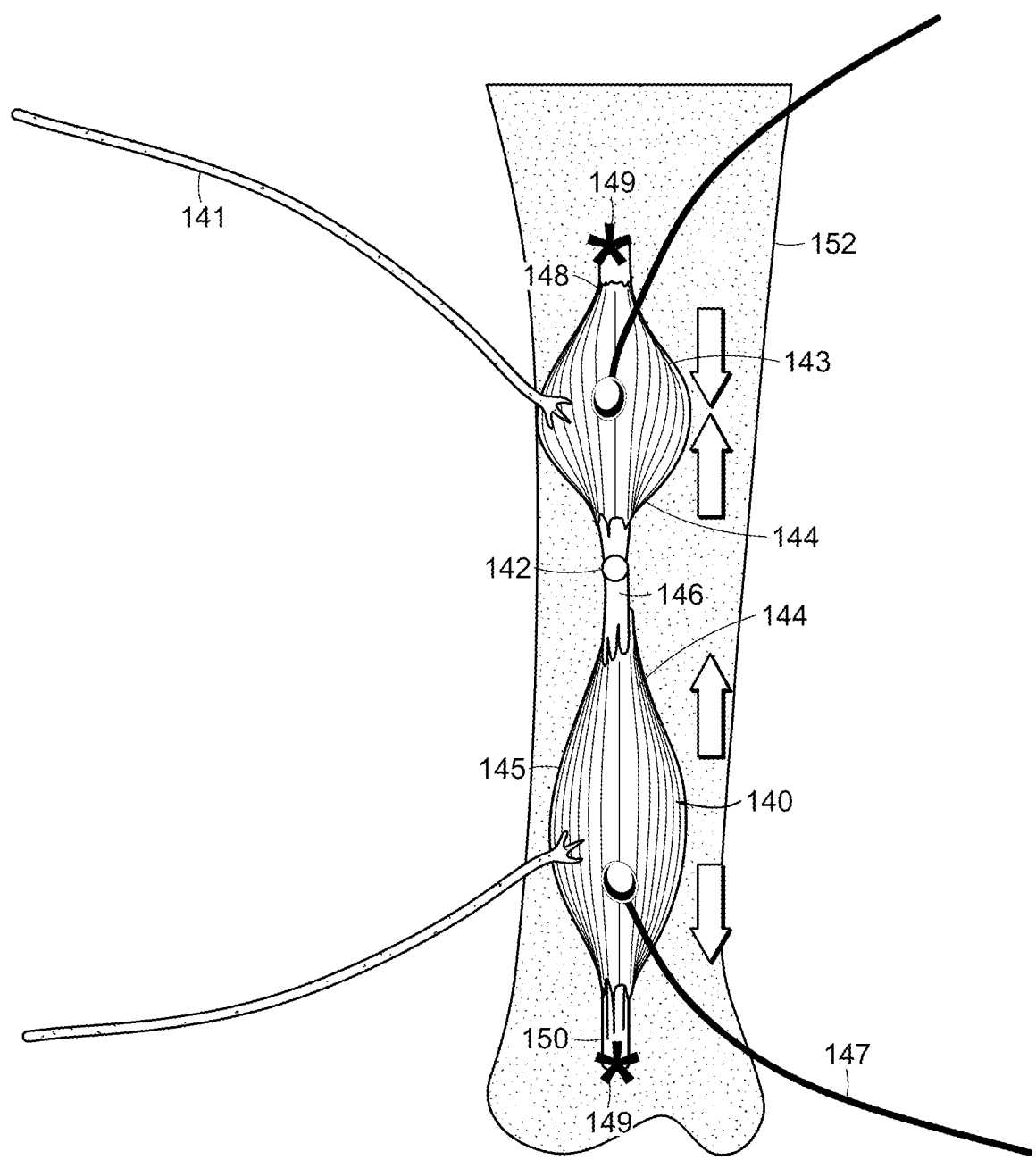
FIG. 15 is a schematic representation of a proprioceptive muscle Regenerative Peripheral Nerve Interface (Pro-m-RPNI) comprising an agonist-antagonist muscle pair series secured to bone or another biological structure at either end, suitable for employment in one embodiment of the method of the invention.
Figure 16:
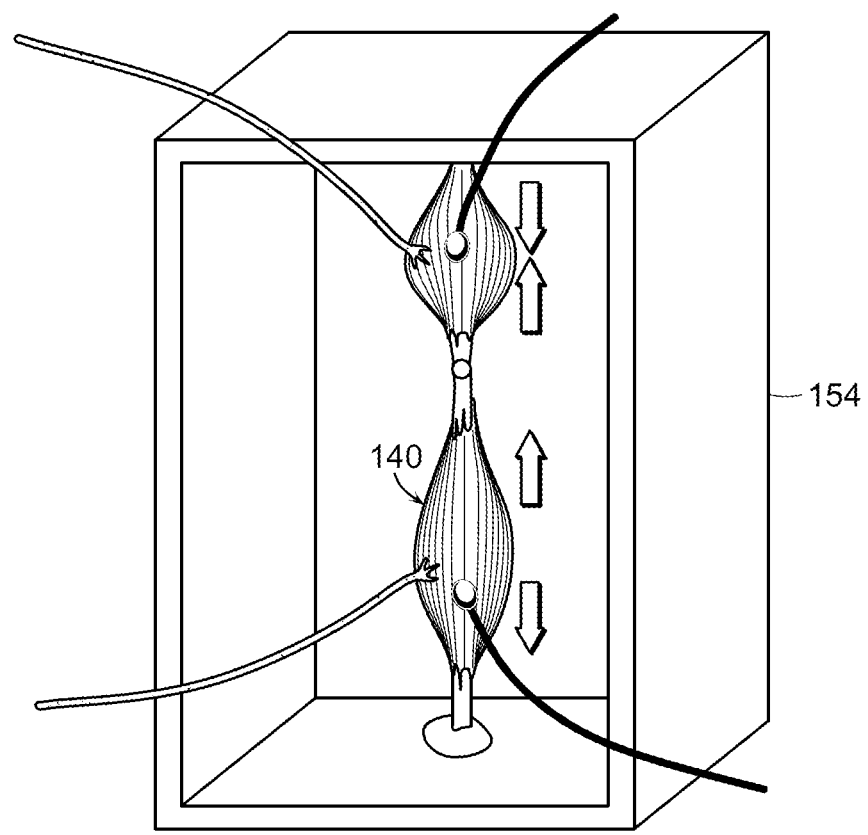
FIG. 16 a schematic representation of a linear Pro-m-RPNI in which the native tendon-bone junction at either end of the series is preserved to enable attachment to a synthetic structure.
Figure 17:
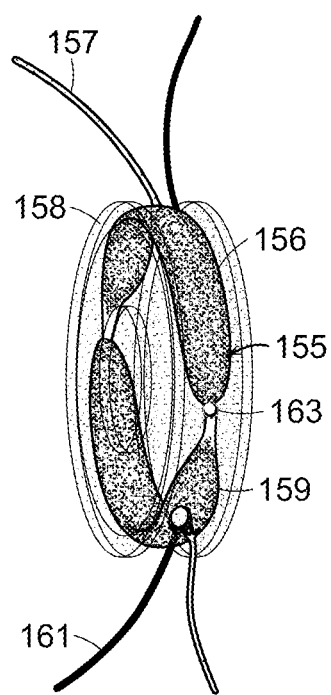
FIG. 17 is a schematic representation of a Pro-m-RPNI secured about a synthetic spool shown comprising: 1) a synthetic spool; 2) an agonist muscle; 3) an agonist motor/afferent nerve; 4) an agonist electrode for electromyographic sensing and functional electrical stimulation; 5) agonist muscle spindle fibers; 6) an agonist Golgi tendon organ; 7) an antagonist muscle; 8) an antagonist motor/afferent nerve; and 9) an antagonist electrode for electromyographic sensing and functional electrical stimulation.

The Pro-m-RPNI structures of FIGS. 15-17 can also employ fascicle position and speed sensors. For example, sonomicrometer crystals can be stitched into muscle fibers (J. A. Hoffer, A. A. Caputi, I. E. Pose, R. I. Griffiths, Prog. Brain Res. 80, 75 (1989)). Sonomicrometry has been used successfully to measure skeletal muscle length changes in situ and during walking in cats, J. A. Hoffer, A. A. Caputi, I. E. Pose, R. I. Griffiths, Prog. Brain Res. 80, 75 (1989), and running in turkeys, T. J. Roberts, R. L. Marsh, P. G. Weyand, C. R. Taylor, "Muscular force in running turkeys: the economy of minimizing work," *Science*, 275 (5303), 1997, 1113-1115. Sonomicrometry is a technique of measuring the distance between piezoelectric crystals based on the speed of acoustic signals through the medium for which they are embedded, the medium for this invention being muscle tissue. Typically, the crystals are coated with an epoxy and placed into the muscle facing each other. An electrical signal sent to either crystal will be transformed into sound, which passes through the tissue, eventually reaching the other crystal, which converts the sound into an electric signal, detected by a receiver. From the time taken for sound to move between the crystals and the speed of sound through tissue, the distance between the crystals can be calculated, or the displacement of a muscle fiber.

When the fiber contracts or is stretched, the relative position of the crystals can thus be measured, and the fiber length determined. Such a measurement of fascicle state can be used in the bi-directional control of a bionic limb. Pro-m-RPNI measured state information can be used to control bionic joint state; as the agonist contracts and the antagonist is stretched, or vice versa, the agonist/antagonist lengths and speeds can be used as control targets by the external bionic limb controller to output corresponding bionic limb joint positions and speeds. However, to accurately estimate joint state, both the length of the muscle fibers and the tendon length must be determined. Tendon length can be estimated from the force applied on the tendon and its stiffness. To determine muscle-tendon force, a muscle model (e.g. Hill muscle model) can be used. Running on the micro-computers on the external bionic limb, a muscle model can estimate the forces borne by the Pro-m-RPNI agonist/antagonist muscles using sensory inputs of muscle EMG levels and fascicle positions and speeds. Alternatively, to attain muscle force sensory information from the Pro-m-RPNI muscles, a force sensor can be implanted as part of the Pro-m-RPNI device. For example, strain gauge sensors 149 can be applied near the tendon-bone interface, shown in FIG. 15, of the various Pro-m-RPNI configurations. Strain gauges (e.g. Tokyo Sokki Kenkyujo Ltd.) can be glued to the internal and external aspects of the free calcified tendon with the use of methods developed for bone (A. A. Biewener, Biomechanics: Structures and Systems (Oxford Univ. Press, Oxford, (1992)). Also, force buckles can provide measurements of forces in individual muscles (B. Walmsley, J. A. Hodgson, R. E. Burke, J. Neurophysiol. 41, 1203 (1978)), and could be employed for this neural interface device.

Alternatively, FES control applied by the external bionic limb controller can exert a position control on the agonist/antagonist muscles of the Pro-m-RPNI by closing the loop using the measured fascicle states. In the case where an external agent is positioning the external bionic joint, such positions would have to be reflected on the agonist/antagonist muscles in order for the prosthetic user to receive accurate proprioceptive feedback. For example, if another person grasps the bionic hand of the prosthetic user with their hand in order to shake the hand of the prosthetic user, such a handshake may forcibly change the positions of the bionic joints. Bionic joint state sensory information would serve as control position and speed targets for a FES control applied to the Pro-m-RPNI muscles by microprocessors positioned on the bionic limb. For example, if the handshake flexed the bionic wrist, the FES controller would receive bionic wrist state information from a synthetic wrist sensor, and apply an electrical activation to the agonist Pro-m-RPNI muscle proportional to the error between the measured bionic wrist position/speed and the measured position/speed from muscle fiber state sensors, causing the muscle to contract and the antagonist to stretch. The prosthetic user would then experience the position of their bionic wrist as imposed by the handshake through an afferent feedback to the spinal cord from muscle spindle receptors in the agonist/antagonist pair.

Therefore, the methods of the invention for simulating a proprioceptive sensory organ for a human limb or organ can variously include the following specific embodiments. In one embodiment, the method includes the step of mechanically linking a plurality of pairs of agonist and antagonist muscles to at least one degree of freedom of the prosthesis, orthosis or exoskeleton. In another embodiment, the method further includes the step of associating a plurality of pairs of electromyographic electrodes, each pair of electromyographic electrodes being electrically connected to a pair of agonist and antagonist muscles, with a plurality of degrees of freedom of the prosthesis orthosis or exoskeleton, each degree of freedom of the prosthesis, orthosis or exoskeleton being associated with at least one pair of electromyographic electrodes of an agonist/antagonist muscle pair. In yet another embodiment, at least one pair of the linked agonist/antagonist muscles is supported by a biological structure, such as a human bone. Alternatively, or additionally, at least one pair of the linked antagonist/antagonist muscles is supported by an artificial support. In a specific embodiment, the agonist/antagonist muscles of the pair are linked linearly to each other at one end, and linked at their respective free ends to the artificial support. At least one of the respective free ends of the agonist/antagonist muscle pair includes native bone, which bone can be secured to the artificial support. In another embodiment, the agonist/antagonist muscles of the pair are linked to each other by the artificial support. In one embodiment, the artificial support is a lever, in which one end of each muscle is attached to an arm, the arms being on opposite sides of a fulcrum of the lever, whereby contraction of one muscle of the agonist/antagonist pair causes extension of the other muscle of the agonist/antagonist pair. In another embodiment, the ends of each agonist/antagonist muscle pair are linked to each other to form a closed loop, and the muscle extends about a periphery of the artificial support, whereby contraction of one of the muscles of the pair will cause extension of the other muscle of the pair. A particular method of the invention further includes the step of implanting in at least one agonist/antagonist muscle pair at least one member of the group consisting of a force sensor and a position sensor. The position sensor can include, for example, a plurality of piezoelectric crystals, such as sonomicrometer crystals. In a specific embodiment of the method of the invention, the relative positions of the implanted crystals are employed to establish a control target of speed and length of the agonist/antagonist muscle pair by the controller to thereby estimate the joint state of the prosthesis, orthosis or exoskeleton. Estimating the joint state can further include the steps of measuring the force applied and the stiffness of a tendon component of at least one of the muscles of the agonist/antagonist muscle pair, and combining those measurements with the measurements of speed and length of the corresponding muscles of the muscle pair wherein the force sensor includes at least one of a strain gauge and a force buckle. A motor controller 182 (see, e.g., FIG. 20 and accompanying description) can employ the strength of an electromyographic sensory signal measured at the agonist/antagonist muscle pairs, and position and speed of the agonist/antagonist muscle pairs to estimate joint state. In another embodiment, the motor controller can detect motion in the prosthesis, orthosis or exoskeleton, and relay that information by selectively stimulating at least one muscle of the agonist/antagonist pair, thereby causing the individual wearing the prosthesis, orthosis or exoskeleton to sense the change in position of the prosthesis, orthosis or exoskeleton.

Cutaneous RPNIs

In yet another embodiment, the invention is directed to simulating a cutaneous sensory organ for a human limb or organ of an individual by excising a skin segment from a limb or portion of a limb, the skin segment including innervating nerve. The skin segment is linked to at least one muscle having a nerve supply, and an electrode is implanted in at least one muscle. The skin segment and actuator muscle are supported on a support. The electrodes are electrically connected to a sensory controller of a device, such as prosthesis, orthosis or exoskeleton, and the controller is linked to a sensor of the device. The controller detects application of at least one member selected from the group consisting of stress, strain, contact, pressure and sheer at the device, and transmits detection of the stress, strain, contact, pressure or sheer by contracting the actuator muscle with the electrode, thereby stretching the mechanoreceptor of the skin segment and providing the individual with a sensation simulating cutaneous sensation at the limb.

In a specific embodiment, at least one pair of agonist and antagonist muscles are mechanically linked, and wherein a nerve innervates each muscle. In one embodiment, at least one muscle of at least a portion of the muscle pairs includes at least one member selected from the group consisting of a Golgi tendon organ, muscle spindle stretch fibers, and an efferent/afferent nerve. At least one pair of agonist and antagonist muscles are supported, whereby contraction of a muscle of each pair will cause extension of the paired muscle. In one embodiment, the Golgi tendon organ of the agonist muscle and the muscle spindle fibers of the antagonist muscle will generate afferent signals. An electrode is implanted in each of the agonist and antagonist muscles of each pair. In one embodiment, each electrode senses and stimulates muscle contraction. The electrodes are electrically connected to a motor controller of a device. In one embodiment, the device includes at least one member selected from the group consisting of a prosthesis, an orthosis and an exoskeleton. In one embodiment, a position about a degree of freedom of the prosthetic, orthotic or exoskeleton can be sensed by an individual wearing the prosthesis, orthosis or exoskeleton, thereby functioning as an artificial proprioceptive sensory organ for a human limb or organ.

In one embodiment, the invention is a method for simulating cutaneous sensory feedback from the device, including steps of excising a skin segment from a biological body part of an individual, the skin segment including at least one of a native nerve and a regenerative nerve supply. The skin segment is linked to at least one muscle having a nerve supply. An electrode is implanted in the at least one muscle. The skin segment and actuator muscle are supported on a support. The at least one electrode is electrically connected to a sensory controller of a device, wherein the controller is linked to a sensor of the device that detects application of at least one of stress, strain, contact, pressure and sheer at the device, and whereby the controller transmits detection of the stress, strain, contact, pressure or sheer by contracting the actuator muscle within electrical stimulation via the electrode, thereby stretching the mechanoreceptor of the skin segment and providing the individual with a sensation stimulating cutaneous sensory feedback from the device.

Figure 18:
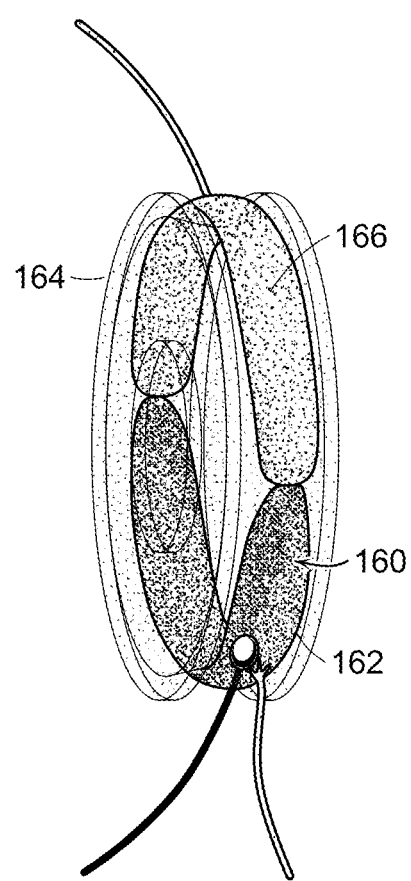
FIG. 18 is a schematic representation of a unidirectional Cutaneous Sensory RPNI (Cut-s-RPNI).
Figure 19:
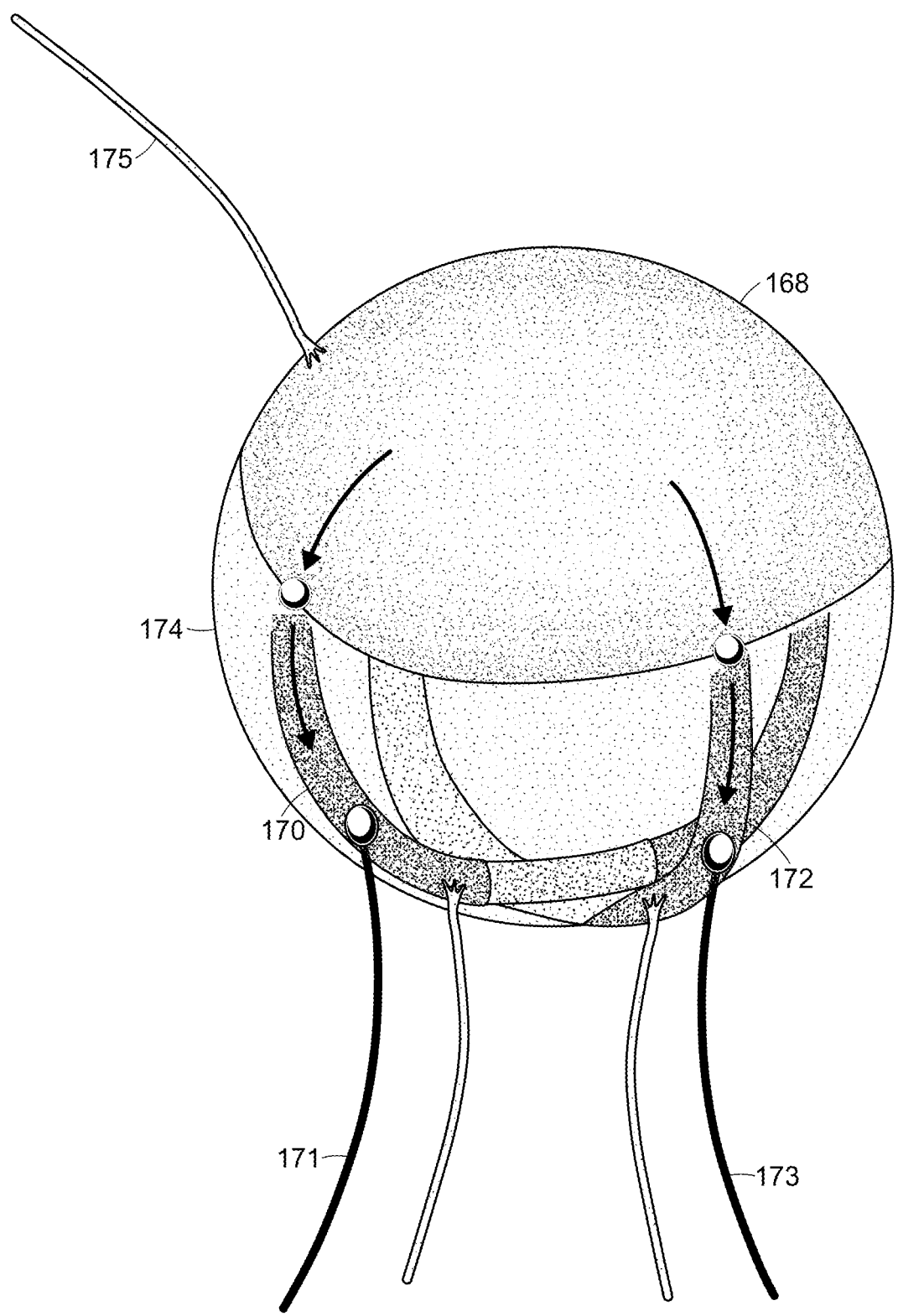
FIG. 19 is a schematic representation of a multi-directional Cut-s-RPNI around a synthetic sphere that is suitable for use in at least one method of the invention.

As can be seen in FIG. 18, Cutaneous Sensory RPNIs (Cut-s-RPNI) 160 may be assembled in a similar manner to the previously described Pro-m-RPNIs to achieve controllable skin strain feedback signals from implanted biological skin mechanoreceptors. Specifically, Cut-s-RPNIs can be constructed so as to incorporate a motor RPNI 162 in series with an innervated strip of de-epithelialized skin 166 around a central, low friction synthetic spool 164. In this embodiment, the de-epithelialized skin is a strip of skin 166, and is attached to the actuator muscle at opposite ends of the strip. The artificial support is a spool 164 and the de-epithelialized skin 166 and actuator muscle are supported about the periphery of the spool 164. To achieve multi-directional skin strain feedback, Cut-s-RPNIs may also be constructed by attaching a skin patch 168 to multiple motor RPNIs 170,172 around a low friction synthetic sphere 174, as shown in FIG. 19. In this embodiment, the artificial support is spherical and the de-epithelialized skin is linked to two actuator muscles that, when contracted, provide tension to the de-epithelized skin in different directions, each actuator muscle being implanted with a separate electromyographic electrodes 171,173 respectively controlled independently by the controller (not shown). Measurements of orthogonal strain (pressure) and tensile shear strain from prosthetic limb sensors will determine FES control commands resulting in contraction of the muscle via electrode signaling, which will, in turn, produce proportional stretch and pressure across the innervated skin strip. Activation of native mechanoreceptors in the skin strip will provide cutaneous sensory feedback through the sensory nerve 175 associated with the skin strip via standard afferent pathways. It will be understood by those of ordinary skill in the art that the spool and sphere structures shown in FIG. 18 can be modified to include non-circular cross sections such as oval cross sections (not shown). The exact shape of these structures can be varied to adjust the relationship between skin pressure and tensile stretch when the muscle(s) contract(s). Similar to the Pro-m-RPNI device described earlier, the muscle(s) of the Cut-s-RPNI can employ implanted sensors that directly measure its fascicle states and forces. As stated earlier, Sonomicrometry can be used to measure fiber length and speed, and strain gauges or force buckles can be used to measure muscle-tendon force. Processors on the external bionic limb can then apply a closed loop control on the skin patch of the Cut-s-RPNI so as to apply controlled skin strains, pressures and shear forces reflecting measured target skin strains, pressures and shear forces recorded by the external prosthetic sensors.

Figure 20:
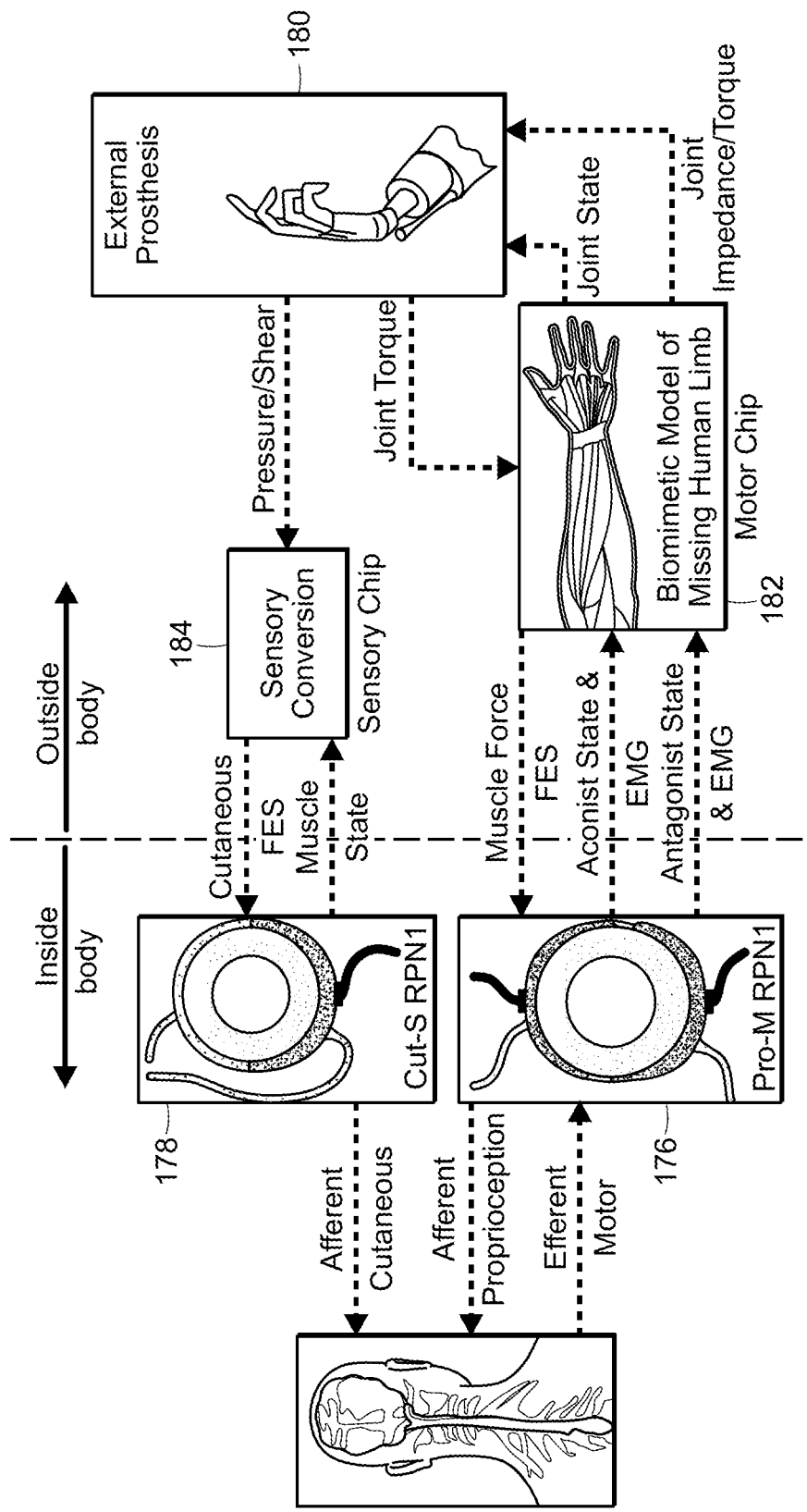
FIG. 20 is a schematic representation of a Pro-m-RPNI and a Cut-s-RPNI integrated with a bionic prosthesis.

Control integration of the Pro-m-RPNI 176 and Cut-s-RPNI 178 devices with an external bionic prosthesis 180 is illustrated in FIG. 20. In this embodiment, the method further includes motor controller 182 that uses a biomechanical model of the missing limb to map the state (fascicle length and speed) and EMG of the agonist/antagonist muscles within the Pro-m-RPNI 176 into a corresponding joint state (angle and angular rate) and joint torque/impedance of the associated degree of freedom within the bionic prosthesis 180. The motor controller 182 then applies a feedback control using the biomimetic joint state and torque/impedance as control targets. Further, motor controller 182 also feedbacks force by measuring torque at the associated bionic prosthesis 180 degree of freedom, mapping that torque to corresponding muscle-tendon forces, and then applying a functional electrical stimulation (FES) control on the muscle that applies a joint torque in the same direction as the measured applied torque thereby modulating the force on the muscle oriented to counter the measured torque. For example, for a measured extension torque at a bionic limb degree of freedom, a FES control is applied on the muscle that is associated with joint extension, thereby modulating the force borne by the opposing muscle that is associated with joint flexion, providing the prosthetic user a direct force feedback from the bionic limb via Golgi tendon organ sensing.

FIG. 20, also depicts a sensory controller 184. This controller maps measured force and shear from the prosthetic sensors into FES signals on the muscle, or muscles, that exert forces on the skin patch of the Cut-s-RPNI. The sensory controller 184 modulates the FES signal until the fascicle state of the Cut-s-RPNI muscle, and corresponding skin force/shear on the Cut-s-RPNI skin patch, are achieved based upon the target force/shear measured from the external prosthesis 180. Through the sensory controller 184, a realistic cutaneous feedback is achieved from the bionic prosthesis 180.

The specific example of a prosthetic user reaching for a bar bell, grasping the bar bell, and then doing a wrist curl is provided to explain the efferent/afferent bi-directional control of the bionic limb 180 described in FIG. 20. The prosthetic user sees the bar bell and decided to reach and grasp it. Upon reaching, descending efferent motor commands activate the agonist and antagonist muscles of the Pro-m-RPNI 176 corresponding the wrist flexors/extensors. For purposes of this example, only the bionic wrist is described, but it should be understood that each degree of freedom of the bionic limb would be controlled by at least one Pro-m-RPNI. A plurality of Pro-m-RPNI devices could be used to control a single degree of freedom if a modulated joint impedance control were sought. Similar to the human body where often multiple agonist-antagonist pairs span a single joint, so too multiple Pro-m-RPNI's can be employed to control a single bionic degree of freedom.

The respective nerve supply for the agonist and antagonist transmit proprioceptive information as an afferent signal to the user's spinal cord. Golgi tendon organs transmit forces while spindle fibers transmit speeds and displacements allowing the prosthetic user to feel their synthetic wrist stiffen and position itself for proper orientation to grasp and manipulate the bar bell.

Further, agonist/antagonist Pro-m-RPNI muscle activations and fascicle states are recorded via electrodes and fiber sonomicrometer crystals, respectively, and sent wirelessly to processing modules located on the bionic limb referred to in FIG. 20 as the motor controller 182. Such signals might also be transmitted directly through wires passing through an osseo-implant to the external bionic limb. A biomimetic model of the missing human limb is then used by the bionic limb controller to map Pro-m-RPNI agonist/antagonist muscle state and EMG levels to corresponding muscle forces using a skeletal muscle model such as the Hill model. In an alternate embodiment, an implanted force sensor directly measures agonist/antagonist force levels, and that sensory information is communicated to the external bionic limb micro-processors. Once the modeled muscle-tendon forces and states are estimated, the biomimetic limb model is then used to map these muscle forces and states to the resulting wrist torque, impedance and joint state of the prosthetic wrist, by conducting a geometric transformation using joint moment arm and joint position information. The biomimetic limb model computes control targets for the bionic limb wrist controller with target wrist torque, impedance and joint state. A closed-loop controller running on the motor controller 182 then servos to such targets. Thus, through neural control, the prosthetic user can control the prosthetic wrist's position, torque and impedance while feeling the movement of the prosthetic wrist through afferent signaling from spindle fibers within the agonist/antagonist Pro-m-RPNI.

Through FES on the Pro-m-RPNI 176 muscles, force and state sensory information can be transmitted into the nervous system. For example, once the bionic hand grasps the bar bell (via control from finger Pro-m-RPNIs), the user contracts the agonist (corresponding to wrist flexor), stretching the antagonist, and providing the sensation of wrist movement. As load from the bar bell is applied to the bionic limb, the antagonist muscle can be activated with a FES control, increasing the force exerted on the contracting agonist muscle proportional to the estimated force exerted by the modeled wrist flexors of the biomimetic model necessary to achieve the measured wrist joint torque levels. Through this force feedback, the prosthetic user can feel the weight of the bar bell as it is being lifted throughout the wrist curl. In another embodiment, FES control can be used to position the agonist/antagonist muscles within the Pro-m-RPNI 176 to reflect measured joint positions of the bionic limb into actual fascicle states of the agonist/antagonist muscles. Generally, such a FES control would occur when, for example, an external agent positions the bionic limb joint, such as during a hand shake, or when the bionic leg strikes the ground surface in a walking/running stride, causing the bionic leg joints to rotate.

Another microprocessor, called the Sensory controller 184 in FIG. 20, located within the bionic limb maps measured strain sensory signals from the synthetic skin of the prosthetic hand into FES control commands applied to the muscle(s) of implanted Cut-s-RPNI(s) 178. To provide a simple example, we assume that each finger digit corresponds to one unidirectional Cut-s-RPNI 178 (See FIG. 18). When the bionic hand grasps the bar bell, the measured orthogonal strain on each synthetic fingertip, or pressure, is converted by the sensory controller 184 into a corresponding cutaneous FES control command. The muscle of the corresponding unidirectional Cut-s-RPNI 178 then contracts and applies a unidirectional tensile strain on the biological skin patch. Because the skin patch wraps around a curved surface, as in FIG. 18, the applied tensile shear also causes an orthogonal shear to be applied to the skin patch, or a pressure. With the coupling between tensile strain and orthogonal strain (pressure) known, the FES on the Cut-s-RPNI 178 muscle is modulated in a closed-loop manner until the measured muscle strain, determined from sonomicrometer crystals implanted within the Cut-s-RPNI 178 muscle, is equal to a target tensile skin strain and a target pressure. The nerve innervating the skin patch then communicates an afferent signal via the skin mechanoreceptors, providing a natural cutaneous feedback into the nervous system and allowing the prosthetic user to better manipulate objects of interest such as the bar bell. The spool shape in FIG. 18, or the sphere shape in FIG. 19, can be adjusted to modulate the relationship between skin tensile shear and orthogonal shear (pressure). Although circular cross sections are shown in FIGS. 18 and 19, more of a point pressure may be sought when a tensile strain is applied to the skin patch, necessitating a non-circular cross section such as an ellipse.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A prosthesis, orthosis or exoskeleton device for restoring lost functionality to a subject, comprising:
   an implanted sensing system configured to measure muscle-tendon signals of at least one agonist-antagonist muscle-tendon pair of the subject, the pair comprising an agonist muscle-tendon connected to an antagonist muscle-tendon, the muscle-tendon signals being representative of agonist-antagonist muscle-tendon dynamics, the muscle-tendon signals comprising at least one of a muscle length, a muscle velocity, or a muscle force in at least one muscle-tendon of the agonist-antagonist muscle-tendon pair;
   a support configured to support the at least one agonist-antagonist muscle-tendon pair, whereby contraction of one muscle-tendon of the at least one pair will cause extension of the paired muscle-tendon; and
   a controller configured to:
   map the muscle-tendon signals to a control target comprising at least one of a joint torque, a joint impedance, or a joint state, the joint impedance comprising at least one of a joint stiffness or a damping, the joint state comprising at least one of a joint angle or an angular rate; and output the control target to command a powered actuator of the prosthesis, orthosis, or exoskeleton device, thereby at least partially restoring the lost functionality to the subject.

2. The device of claim 1, wherein the muscle-tendon signals include the muscle length and the muscle velocity.

3. The device of claim 1, wherein the muscle-tendon signals include the muscle force.

4. The device of claim 1, wherein the implanted sensing system includes at least one of a position sensor or a force sensor implanted at the muscle.

5. The device of claim 4, wherein the implanted sensing system comprises a position sensor and wherein the position sensor includes a plurality of implanted piezoelectric crystals.

6. The device of claim 5, wherein the piezoelectric crystals include sonomicrometry crystals.

7. The device of claim 6, wherein the implanted piezoelectric crystals are each configured to define a position relative to at least one other of the implanted piezoelectric crystals, and wherein the controller maps the relative positions of the crystals to the control target.

8. The device of claim 7, wherein the implanted sensing system comprises a force sensor, and wherein estimating the joint state further includes measuring with the force sensor the force applied by the muscle, and combining that measurement with the measurement of at least one of speed or length of the muscle.

9. The device of claim 8, wherein the force sensor includes at least one of a strain gauge or a force buckle.

10. The device of claim 4, wherein the controller maps at least one of i) force estimated using measurement of at least one of length or speed of the muscle measured with the position sensor, or ii) force measured with the force sensor, to the control target.

11. The device of claim 10, wherein the controller maps to the control target a muscle model estimate of the tendon force using the measurement of the at least one of length or speed of the muscle and an electromyographic signal strength measured at the muscle.

12. The device of claim 11, further comprising an electrode implanted at the biological muscle, the electromyographic signal strength being measured with the electrode.

13. The device of claim 12, wherein the electrode is implanted on an epimysium of the muscle or intramuscularly in the muscle.

14. The device of claim 1, wherein the controller is configured to receive joint position or joint torque signals from the prosthesis, orthosis or exoskeleton device, and to map the signals to a functional electrical stimulation channel that stimulates at least one muscle of the agonist and antagonist muscle pair via an associated pair of electrodes, delivering proprioceptive feedback to the subject wearing the device.

15. The device of claim 14, wherein the controller employs a biomimetic model of the limb to map measured joint torque of the prosthesis, orthosis or exoskeleton device to corresponding muscle-tendon forces of the agonist and antagonist muscle pair, and wherein the controller is configured to selectively stimulate the at least one muscle of the agonist and antagonist muscle pair that is associated with joint torque in the same direction as the measured joint torque, thereby modulating force on other muscle of the agonist and antagonist muscle pair.

16. The device of claim 1, wherein the controller employs a biomimetic model of the limb to map the measured muscle state of at least one muscle of the agonist and antagonist muscle pair and an electromyographic signal strength measured at the at least one muscle to a corresponding joint state and joint torque of the device.

17. The device of claim 1, further comprising a sensory controller that maps detection of at least one of stress, strain, contact, pressure, force, or shear applied at the device into electrical stimulation of an actuator muscle coupled to and exerting forces on a skin patch of the subject, to provide the subject with cutaneous sensory feedback from the device.

18. The device of claim 1,
further comprising a pair of electrodes, one electrode of the pair of electrodes operatively connected to the agonist muscle or an agonist nerve and the other electrode of the pair of electrodes operatively connected to the antagonist muscle or an antagonist nerve of the at least one agonist-antagonist muscle-tendon pair, and the controller further comprising at least one pair of functional-electrical stimulation (FES) channels, the pair of FES channels operatively connected to the electrodes and mapped to a prosthetic joint state or torque associated with the agonist-antagonist muscle-tendon pair; the controller configured to apply simulation via the FES channels to control at least one of muscle-tendon force or muscle-tendon position so as to provide proprioceptive feedback to the subject that is representative of feedback applied in an intact limb prior to amputation from the same loading conditions.

19. The device of claim 1, wherein the controller applies closed-loop control of an actuator of the prosthesis, orthosis or exoskeleton device, the actuator servoing to the control target, thereby at least partially restoring the lost functionality to the subject.

20. The device of claim 1, wherein the sensing system comprises a plurality of position sensors implanted in the at least one muscle-tendon of the agonist-antagonist muscle-tendon pair; and, the relative positions of the plurality of position sensors is used to measure muscle contraction or elongation, the muscle contraction or elongation is then used to estimate at least one of muscle length, muscle velocity, or muscle force, the at least one of muscle length, muscle velocity, or muscle force is used to map to the control target.

21. The device of claim 1, wherein the support comprises synthetic material.

22. The device of claim 1, wherein the support comprises biologic material.

23. The device of claim 1, wherein the support is configured to support the at least one agonist-antagonist muscle-tendon pair at opposite ends of the support.

* * * * *